United States Patent
Miyoshi

(10) Patent No.: US 10,254,530 B2
(45) Date of Patent: Apr. 9, 2019

(54) IMAGING APPARATUS, MICROSCOPE SYSTEM, IMAGING METHOD, AND COMPUTER-READABLE RECORDING MEDIUM

(71) Applicant: OLYMPUS CORPORATION, Tokyo (JP)

(72) Inventor: Takashi Miyoshi, Atsugi (JP)

(73) Assignee: OLYMPUS CORPORATION, Tokyo (JP)

( * ) Notice: Subject to any disclaimer, the term of this patent is extended or adjusted under 35 U.S.C. 154(b) by 394 days.

(21) Appl. No.: 15/065,010

(22) Filed: Mar. 9, 2016

(65) Prior Publication Data

US 2016/0187638 A1 Jun. 30, 2016

Related U.S. Application Data

(63) Continuation of application No. PCT/JP2014/071395, filed on Aug. 13, 2014.

(30) Foreign Application Priority Data

Sep. 13, 2013 (JP) .................................. 2013-190820

(51) Int. Cl.
  *G02B 21/36* (2006.01)
  *G02B 21/06* (2006.01)
  (Continued)

(52) U.S. Cl.
  CPC ........... *G02B 21/367* (2013.01); *G02B 21/06* (2013.01); *G02B 21/16* (2013.01);
  (Continued)

(58) Field of Classification Search
  CPC ... G02B 21/367; G02B 21/06; G02B 27/0927
  (Continued)

(56) References Cited

U.S. PATENT DOCUMENTS 8,000,560 B2  8/2011  Shirota
8,363,099 B2  1/2013  Fujiyoshi
(Continued)

FOREIGN PATENT DOCUMENTS

JP  2007-065669 A  3/2007
JP  2008-191427 A  8/2008
(Continued)

OTHER PUBLICATIONS

International Search Report dated Nov. 18, 2014 issued in PCT/JP2014/071395.
(Continued)

*Primary Examiner* — Jeffery A Williams
(74) *Attorney, Agent, or Firm* — Scully, Scott, Murphy & Presser, P.C.

(57) ABSTRACT

An imaging method including: controlling luminance distribution of light such that the light continuously attenuates from an inner side toward an edge in a peripheral area within an imaging range of an imaging unit; emitting, in the imaging range, the light whose luminance distribution has been controlled; imaging an object within the imaging range where the light has been emitted to generate image data; sequentially moving the imaging range relative to the object such that peripheral areas where the light attenuates overlap with each other in adjacent imaging ranges; sequentially obtaining a plurality of images with different imaging ranges based on the image data; and creating a combined image by stitching the plurality of images in such a way that adjacent images of the plurality of images corresponding to the adjacent imaging ranges are stitched together such that image areas corresponding to the peripheral areas overlap with each other.

14 Claims, 21 Drawing Sheets

(51) Int. Cl.
*G02B 21/00* (2006.01)
*G02B 21/16* (2006.01)
*G02B 27/09* (2006.01)
*G06K 9/52* (2006.01)
*G06T 5/00* (2006.01)
*G06T 7/60* (2017.01)
*H04N 5/265* (2006.01)
*H04N 5/225* (2006.01)
*H04N 5/262* (2006.01)
*G01N 21/64* (2006.01)
*G06K 9/46* (2006.01)

(52) U.S. Cl.
CPC ........... *G02B 27/0927* (2013.01); *G06K 9/52* (2013.01); *G06T 5/00* (2013.01); *G06T 7/60* (2013.01); *H04N 5/2256* (2013.01); *H04N 5/265* (2013.01); *H04N 5/2624* (2013.01); *G01N 21/6458* (2013.01); *G06K 2009/4666* (2013.01)

(58) Field of Classification Search
USPC .......................................................... 348/79
See application file for complete search history.

(56) References Cited

U.S. PATENT DOCUMENTS

| | | |
|---|---|---|
| 2006/0045388 A1 | 3/2006 | Zeineh et al. |
| 2008/0187208 A1* | 8/2008 | Shirota .............. G06K 9/00134 382/133 |
| 2011/0285838 A1 | 11/2011 | Kishima et al. |
| 2012/0092533 A1* | 4/2012 | Komori ................ H04N 5/3658 348/251 |
| 2015/0356727 A1* | 12/2015 | Urano .................. G01N 21/956 382/149 |

FOREIGN PATENT DOCUMENTS

| | | |
|---|---|---|
| JP | 2010-134374 A | 6/2010 |
| JP | 2012-003214 A | 1/2012 |

OTHER PUBLICATIONS

"Kaitei Baiyo Saibo Jikken Handobukku (The cell culture protocols, second edition)" Namho Huh and Yukio Nakamura (Eds.), Yodosha, Published on Jan. 1, 2009, p. 173, together with partial translation.

* cited by examiner

FIG.10
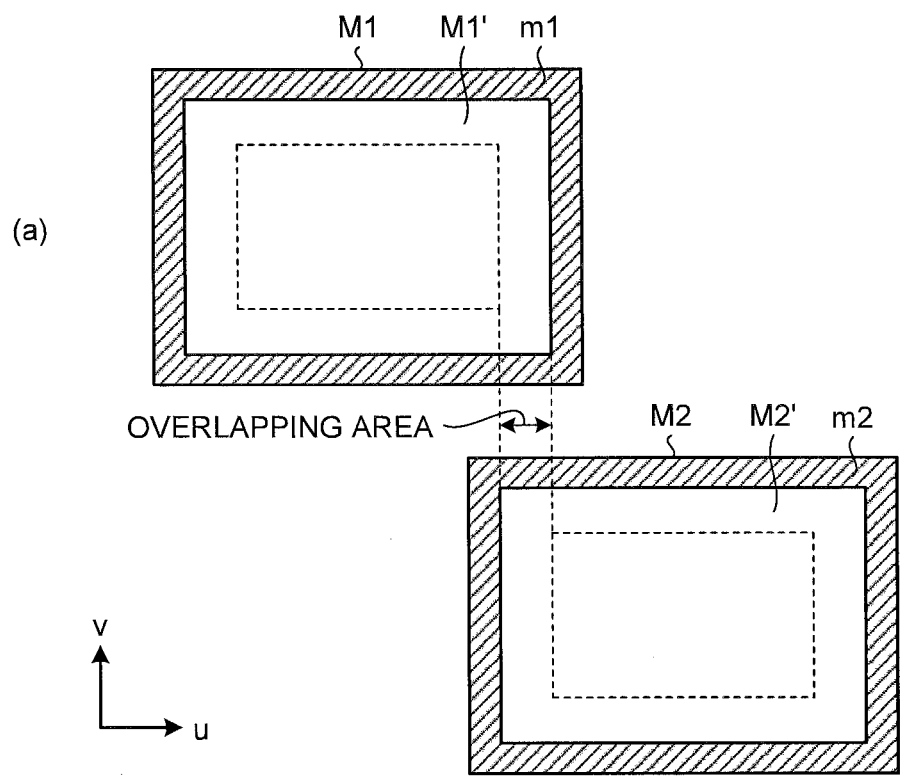
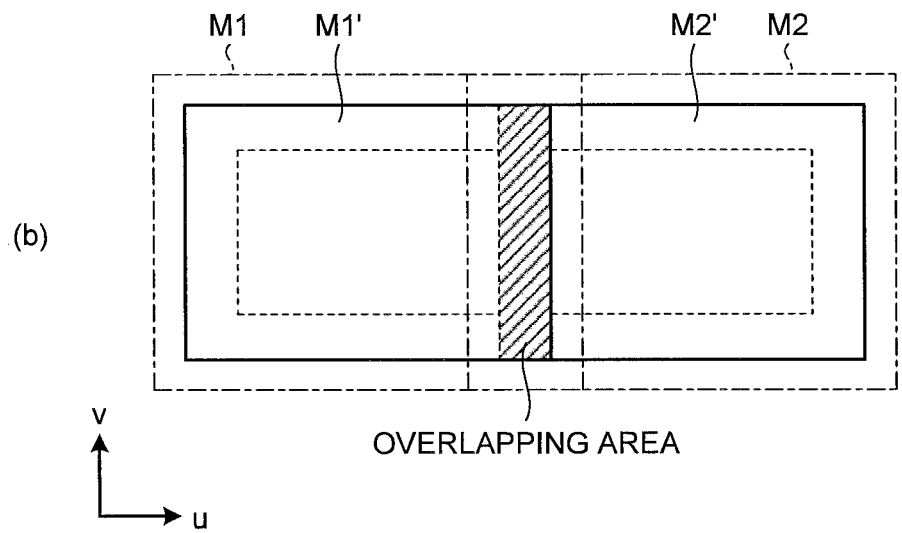

IMAGING APPARATUS, MICROSCOPE SYSTEM, IMAGING METHOD, AND COMPUTER-READABLE RECORDING MEDIUM

CROSS REFERENCES TO RELATED APPLICATIONS

This application is a continuation of PCT international application Ser. No. PCT/JP2014/071395, filed on Aug. 13, 2014 which designates the United States, incorporated herein by reference, and which claims the benefit of priority from Japanese Patent Application No. 2013-190820, filed on Sep. 13, 2013, incorporated herein by reference.

BACKGROUND

1. Technical Field

The disclosure relates to an imaging apparatus, a microscope system, an imaging method, and a computer-readable recording medium, for stitching a plurality of images obtained by imaging a specimen to create a wide-field image.

2. Related Art

In recent years, a virtual slide technique has been known. The virtual slide technique records an image of a specimen placed on a glass slide as electronic data such that a user can observe the image on a monitor of a personal computer, or the like. With the virtual slide technique, partial images of a specimen enlarged by a microscope are sequentially stitched together so as to organize a wide-field high-resolution image of the entire specimen. In other words, the virtual slide technique obtains a plurality of images with different fields of a same object and stitches these images so as to create an enlarged image of the object. Processing to connect a plurality of images is, in some cases, referred to as stitching processing (refer to Japanese Laid-open Patent Publication No. 2012-3214, for example).

Some specimens observed in the fields of biology and medicine are degraded by exposure to light. For example, there are cases in which fading of color occurs on a stained specimen, or health of a cultured cell is impaired by exposure to light. An effect of light like this is also referred to as phototoxicity. To avoid this, the specimen that is degraded by exposure to light is treated such that it is stored in the absence of light and that the minimum required amount of light is emitted in a limited time of imaging (refer to "Kaitei Baiyo Saibo Jikken Handobukku (The cell culture protocols, second edition)" Namho Huh and Yukio Nakamura (Eds.), YODOSHA, Published on Jan. 1, 2009, p. 173, for example).

SUMMARY

In accordance with some embodiments, an imaging apparatus, a microscope system, an imaging method, and a computer-readable recording medium are presented.

In some embodiments, an imaging apparatus includes: an imaging unit configured to image an object within an imaging range to generate image data; an illumination unit configured to generate light to be emitted in the imaging range; an illumination control unit configured to control luminance distribution of the light such that the light continuously attenuates from an inner side toward an edge in a peripheral area within the imaging range; an imaging range movement control unit configured to sequentially move the imaging range relative to the object such that peripheral areas where the light attenuates overlap with each other in adjacent imaging ranges; and a computing unit configured to sequentially obtain, from the imaging unit, the image data of a plurality of images with different imaging ranges and to create a combined image by stitching the plurality of images in such a way that adjacent images of the plurality of images corresponding to the adjacent imaging ranges are stitched together such that image areas corresponding to the peripheral areas overlap with each other.

In some embodiments, an imaging method includes: controlling luminance distribution of light such that the light continuously attenuates from an inner side toward an edge in a peripheral area within an imaging range of an imaging unit; emitting, in the imaging range, the light whose luminance distribution has been controlled; imaging an object within the imaging range where the light has been emitted to generate image data; sequentially moving the imaging range relative to the object such that peripheral areas where the light attenuates overlap with each other in adjacent imaging ranges; sequentially obtaining a plurality of images with different imaging ranges based on the image data; and creating a combined image by stitching the plurality of images in such a way that adjacent images of the plurality of images corresponding to the adjacent imaging ranges are stitched together such that image areas corresponding to the peripheral areas overlap with each other.

In some embodiments, a non-transitory computer-readable recording medium with an executable program stored thereon is presented. The program instructs a processor to execute: controlling luminance distribution of light such that the light continuously attenuates from an inner side toward an edge in a peripheral area within an imaging range of an imaging unit; emitting, in the imaging range, the light whose luminance distribution has been controlled; imaging an object within the imaging range where the light has been emitted to generate image data; sequentially moving the imaging range relative to the object such that peripheral areas where the light attenuates overlap with each other in adjacent imaging ranges; sequentially obtaining a plurality of images with different imaging ranges based on the image data; and creating a combined image by stitching the plurality of images in such a way that adjacent images of the plurality of images corresponding to the adjacent imaging ranges are stitched together such that image areas corresponding to the peripheral areas overlap with each other.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 10 is a schematic diagram for explaining the image stitching processing illustrated in FIG. 9;

DETAILED DESCRIPTION

Hereinafter, exemplary embodiments of an imaging apparatus, a microscope system, an imaging method, and a computer-readable recording medium will be described in detail with reference to the drawings. In the following, an exemplary imaging apparatus according to the present invention will be described as an embodiment of the microscope system that includes a microscope apparatus provided with an imaging unit and a control apparatus. The present invention, however, is not limited to the embodiments. The present invention is applicable to various types of apparatuses having an imaging function. The same reference signs are used to designate the same elements throughout the drawings.

First Embodiment

Figure 1:
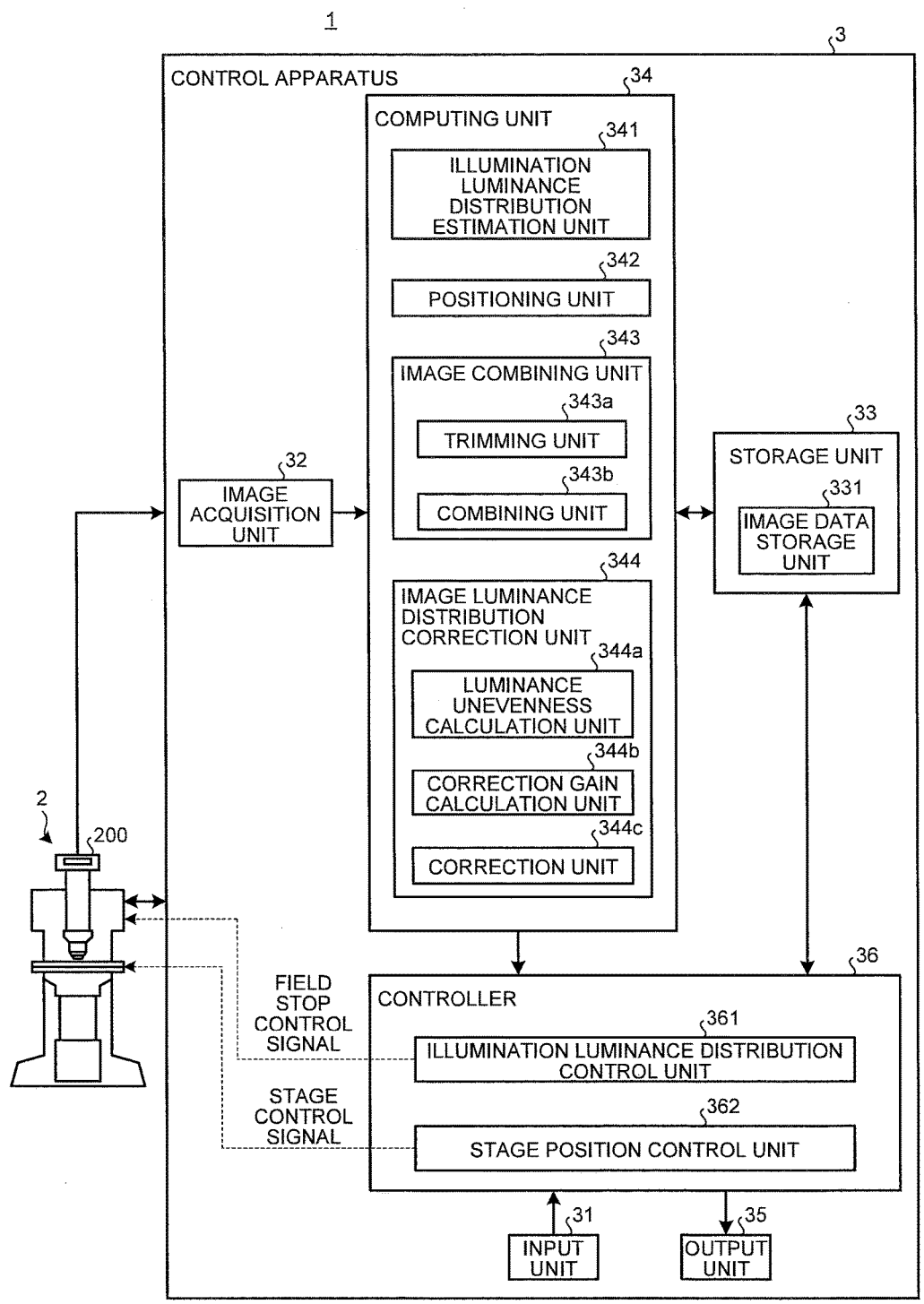
FIG. 1 is a block diagram of an exemplary configuration of a microscope system according to a first embodiment of the present invention.

FIG. 1 is a diagram of a microscope system according to a first embodiment of the present invention. As illustrated in FIG. 1, a microscope system 1 according to the first embodiment includes a microscope apparatus 2 having an imaging unit 200, and a control apparatus 3 that controls operation of the microscope apparatus 2 and that obtains image data from the imaging unit 200 and performs specified calculation processing on the obtained image data.

Figure 2:
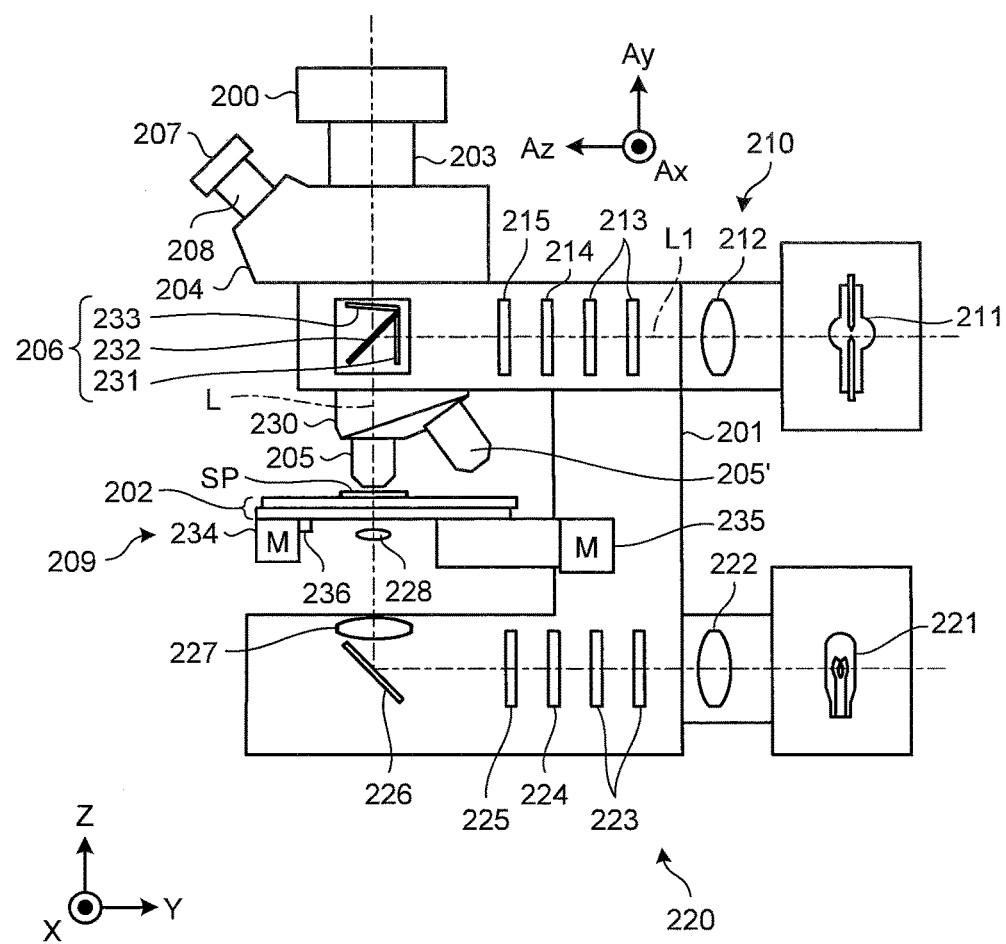
FIG. 2 is a schematic diagram of a configuration of a microscope apparatus illustrated in FIG. 1.

FIG. 2 is a schematic diagram of a configuration of the microscope apparatus 2. As illustrated in FIG. 2, the microscope apparatus 2 includes an arm 201, a specimen stage 202, a lens barrel 203, a trinocular lens barrel unit 204, an objective lens 205, a fluorescence cube 206, an eyepiece 207, an ocular tube 208, and a stage position changing unit 209. The arm 201 has a substantially C shape and is provided with an epi-illumination unit 210 and a transmitted-light illumination unit 220. The specimen stage 202 is mounted on the arm 201 and a specimen SP, which is an object, is placed on the specimen stage 202. The objective lens 205 is provided on an end of the lens barrel 203 via the trinocular lens barrel unit 204, in such a position that faces the specimen stage 202. The fluorescence cube 206 is provided on an observation light path L. The ocular tube 208 is provided with the eyepiece 207. The stage position changing unit 209 moves the specimen stage 202. The imaging unit 200 is provided on another end of the lens barrel 203. The trinocular lens barrel unit 204 branches observation light for the specimen SP incident from the objective lens 205 into directions of the imaging unit 200 and of the ocular tube 208.

The epi-illumination unit 210 includes an epi-illumination light source 211 and an epi-illumination optical system. The epi-illumination light source 211 generates an epi-illumination light to irradiate the specimen SP. The epi-illumination optical system guides the epi-illumination light in a direction of the observation light path L. The epi-illumination optical system includes a collector lens 212, an epi-illumination filter 213, an epi-illumination field stop 214, and an epi-illumination aperture stop 215. Among these, each of the epi-illumination field stop 214 and the epi-illumination aperture stop 215 has an aperture adjustment unit for adjusting the amount of aperture opening. The epi-illumination light emitted from the epi-illumination unit 210 changes its optical path at the fluorescence cube 206 and is emitted onto the specimen SP on the specimen stage 202.

Figure 3:
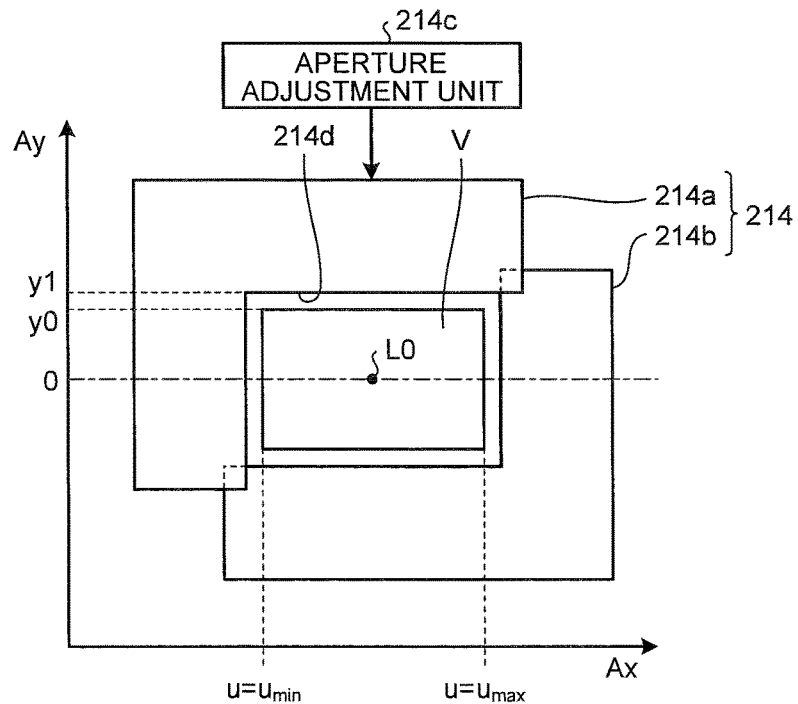
FIG. 3 is a schematic diagram of a configuration of an epi-illumination field stop illustrated in FIG. 2.
Figure 4:
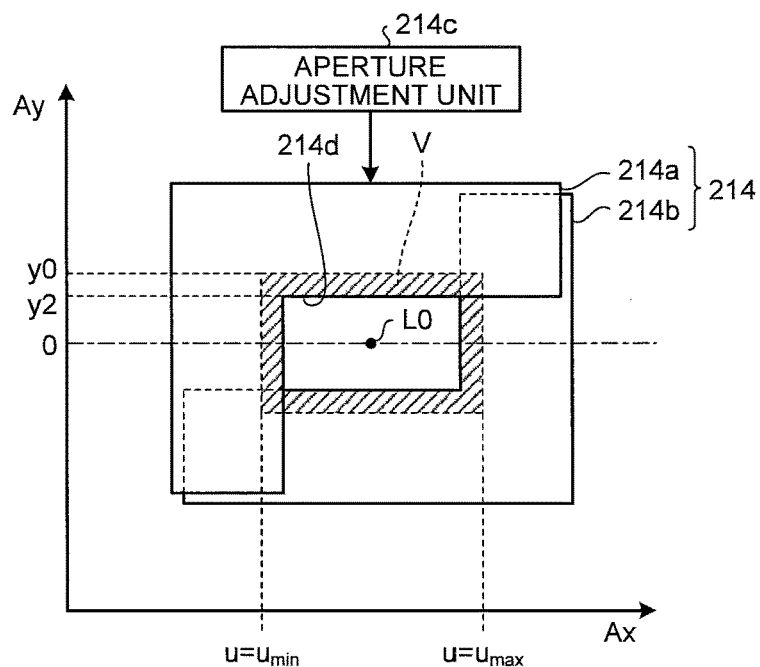
FIG. 4 is a schematic diagram of a configuration of the epi-illumination field stop illustrated in FIG. 2.

Each of FIGS. 3 and 4 is a schematic diagram of a configuration of the epi-illumination field stop 214. Hereinafter, a direction parallel to an optical axis L1 of the epi-illumination optical system is defined as an Az direction and a surface orthogonal to the optical axis L1 is defined as an Ax-Ay surface. To facilitate understanding, FIGS. 3 and 4 are drawn such that an imaging range V of the imaging unit 200 is indicated to be on a same surface of an aperture surface of the epi-illumination field stop 214 and an Ay coordinate corresponding to an upper end of the imaging range V is determined as Ay=y0.

Herein, in the present application, the imaging range represents an area, on the specimen SP surface on the specimen stage 202, to come within a field of the imaging unit 200. A relative coordinates of the imaging range in a case where the position of the specimen SP on the specimen stage 202 is defined as a reference are determined as (u, v).

The epi-illumination field stop 214 includes a square field stop assembled by combining two L-shaped aperture members 214a, and 214b, and an aperture adjustment unit 214c for adjusting the aperture size of the epi-illumination field stop 214. The aperture members 214a and 214b are provided so as to be symmetrical to and movable linked with the optical axis L1, within the Ax-Ay surface. The position of any of the aperture members 214a and 214b is adjusted by the aperture adjustment unit 214c, thereby changing the size of the square-shaped aperture.

FIG. 3 indicates a state in which the aperture size of the aperture member 214a has been set such that an image of an aperture end portion 214d of the aperture member 214a is larger than the imaging range V (Ay=y1, y1>y0). Meanwhile, FIG. 4 illustrates a state in which the aperture size of the aperture member 214a has been set such that an image of the aperture end portion 214d overlaps with a peripheral portion of the imaging range V (Ay=y2, y2<y0). In FIG. 4, areas in which the imaging range V and the aperture members 214a and 214b are overlapping with each other are indicated with hatching patterns.

The transmitted-light illumination unit 220 includes a transmission illumination light source 221 and a transmitted-light illumination optical system. The transmission illumination light source 221 generates transmission illumination light to irradiate the specimen SP. The transmitted-light illumination optical system guides the transmission illumination light in a direction of the observation light path L. The transmitted-light illumination optical system includes a collector lens 222, a transmission filter 223, a transmission field stop 224, and a transmission aperture stop 225. Among these, each of the transmission field stop 224 and the transmission aperture stop 225 has an aperture adjustment unit for adjusting the amount of aperture opening. The configuration of the transmission field stop 224 is similar to the configuration illustrated in FIGS. 3 and 4.

The transmission illumination light emitted from the transmitted-light illumination unit 220 changes its optical path at a reflection mirror 226 and is emitted onto the specimen SP via a window lens 227 and a transmission condenser lens 228.

The objective lens 205 is attached to a revolver 230. The revolver 230 is capable of holding a plurality of objective lenses (objective lenses 205 and 205', for example) with different magnifications. By rotating the revolver 230 to change the objective lenses 205 and 205' facing the specimen stage 202, it is possible to change imaging magnifications.

The revolver 230 includes an encoder. An output value of the encoder is input into the control apparatus 3. Based on the output value of the encoder, the control apparatus 3 is capable of obtaining magnification of the objective lens (objective lens 205, for example) facing the specimen SP, namely, obtaining observation magnification on the microscope apparatus 2.

Furthermore, in order to achieve finer magnification change, there may be provided, inside the lens barrel 203, a zoom unit that includes a plurality of zoom lenses (not illustrated) and a driving unit (not illustrated) for changing positions of the zoom lenses. The zoom unit enlarges or reduces an object image by adjusting the position of each of the zoom lenses. Moreover, there may be provided an encoder in the driving unit inside the lens barrel 203. In this case, the configuration may be such that an output value from the encoder is output to the control apparatus 3, and then, on the control apparatus 3, the position of the zoom lens is detected from the output value from the encoder so as to automatically calculate the imaging magnification.

The fluorescence cube 206 is arranged in the observation light path L when fluorescence observation is performed on the microscope apparatus 2. The fluorescence cube 206 is an optical member having an excitation filter 231, a dichroic mirror 232, and an absorption filter 233 combined in a cube shape. The excitation filter 231 transmits light (excitation light) having a specific wavelength band selectively from among the light beams that have been emitted from the epi-illumination light source 211 and have transmitted through the epi-illumination optical system including the collector lens 212 to the epi-illumination aperture stop 215. The dichroic mirror 232 reflects the light transmitted through the excitation filter 231 to proceed in a direction of the specimen SP, and transmits the light incident from the direction of the specimen SP. The absorption filter 233 transmits the light having a specific wavelength band (fluorescence) selectively from among the light beams incident from the direction of the specimen SP. In a case where transmitted bright field observation is performed on the microscope apparatus 2, the fluorescence cube 206 is moved to a position apart from the observation light path L.

The stage position changing unit 209 includes, for example, motors 234 and 235. Under the control of the control apparatus 3, the stage position changing unit 209 moves a position of the specimen stage 202 within an XY plane so as to relatively move the imaging range with respect to the specimen SP, and moves the specimen stage 202 along the Z-axis so as to cause the objective lens 205 to focus on the specimen SP.

In addition, the stage position changing unit 209 includes a position detection unit 236 that detects a position of the specimen stage 202 and outputs a detection signal to the control apparatus 3. The position detection unit 236 is configured, for example, with an encoder that detects a rotation speed of the motor 234. Alternatively, the stage position changing unit 209 may be configured to include a pulse generation unit that generates a pulse under the control of the control apparatus 3, and a stepping motor.

The imaging unit 200 may be, for example, a camera that includes an image sensor such as a CCD and a CMOS. Specifically, the imaging unit 200 may be a camera capable of capturing a monochromatic image in which a luminance value Y is output as a pixel level (pixel value) on each of pixels provided on the image sensor. Alternatively, the imaging unit 200 may be a camera capable of capturing a color image having a pixel level (pixel value) in each band of R (red), G (green), and B (blue). The imaging unit 200 operates in specified timing under the control by the control apparatus 3. The imaging unit 200 receives light (observation light) incident from the objective lens 205 via the optical system inside the lens barrel 203, generates image data corresponding to the observation light, and outputs the image data onto the control apparatus 3. The configuration may be such that the imaging unit 200 converts the pixel value represented by an RGB color space into the pixel value represented by a YCbCr color space and outputs the value to the control apparatus 3.

Referring back to FIG. 1, the control apparatus 3 includes an input unit 31, an image acquisition unit 32, a storage unit 33, a computing unit 34, an output unit 35, and a controller 36. The input unit 31 is used to input various types of commands and information to the control apparatus 3. The image acquisition unit 32 acquires image data from the imaging unit 200. The computing unit 34 performs specified image processing on the image data acquired by the image acquisition unit 32 and executes various types of calculation processing. The output unit 35 outputs the image on which image processing has been performed by the computing unit 34. The controller 36 integrally controls all these units.

The input unit 31 includes input devices such as a keyboard, various types of buttons, and various types of switches, and pointing devices such as a mouse and a touch panel. The input unit 31 inputs a signal that corresponds to the operation executed externally by a user, to the controller 36.

The image acquisition unit 32 is an interface connectable with an external apparatus such as the imaging unit 200 and sequentially acquires image data generated by the imaging unit 200.

The storage unit 33 is configured to include a recording apparatus including a semiconductor memory such as a rewritable flash memory, a RAM, and ROM, a recording medium including a hard disk, an MO, a CD-R, and a DVD-R, that is either built-in or connected via a data communication terminal, and a recording apparatus including a read/write apparatus for executing read/write of information with the recording medium. The storage unit 33 includes an image data storage unit 331 that stores image data on which image processing has been performed by the computing unit 34.

The computing unit 34 includes an illumination luminance distribution estimation unit 341, a positioning unit 342, an image combining unit 343, and an image luminance distribution correction unit 344. The illumination luminance distribution estimation unit 341 estimates luminance distribution of light to be emitted in the imaging range (hereinafter, also referred to as irradiation light). The positioning unit 342 determines the amount of movement of the specimen stage 202 per imaging on the microscope apparatus 2 (hereinafter, referred to as a stage movement amount), or the like. The image combining unit 343 creates a combined image by stitching a plurality of images with different imaging ranges. The image luminance distribution correction unit 344 corrects luminance distribution on the combined image created by the image combining unit 343.

The illumination luminance distribution estimation unit 341 estimates, based on an image obtained on the microscope apparatus 2 by imaging a reference sample for luminance distribution measurement, luminance distribution of the light to be emitted in observation of the specimen SP, and creates luminance distribution information on the light.

The positioning unit 342 determines the stage movement amount based on the luminance distribution estimated by the illumination luminance distribution estimation unit 341. In addition, based on the stage movement amount, the positioning unit 342 determines a coordinate value of an image area corresponding to an "overlap width" used for stitching adjacent images with each other in the image combining unit 343. Hereinafter, an image area corresponding to the "overlap width" will be referred to as an overlapping area.

The image combining unit 343 creates a wide-field combined image by stitching a plurality of images obtained by sequentially imaging the specimen SP while changing the imaging range. More specifically, the image combining unit 343 includes a trimming unit 343a and a combining unit 343b. The trimming unit 343a trims an area to be used for image combining from each of the images. The combining unit 343b stitches the trimmed images with each other.

Based on the luminance distribution of the irradiation light estimated by the illumination luminance distribution estimation unit 341, the image luminance distribution correction unit 344 corrects luminance distribution on the combined image created by stitching the plurality of images. More specifically, the image luminance distribution correction unit 344 includes a luminance unevenness calculation unit 344a, a correction gain calculation unit 344b, and a correction unit 344c. Based on the luminance distribution of the irradiation light, the luminance unevenness calculation unit 344a calculates luminance unevenness occurring in an overlapping area on which images are stitched together. The correction gain calculation unit 344b calculates a correction gain for correcting the calculated luminance unevenness.

The correction unit 344c corrects the luminance unevenness in the overlapping area of the combined image by using the correction gain.

The output unit 35 is an external interface for outputting the combined image created by the computing unit 34 and other predetermined information to an external apparatuses including an LCD, an EL display, or a CRT display. In the first embodiment, the display apparatus for displaying the combined image, or the like, is provided outside the microscope system 1. Alternatively, however, the display apparatus may be provided inside the microscope system 1.

The controller 36 integrally controls overall operation of the microscope system 1, based on various types of commands input from the input unit 31 and various types of information input from the microscope apparatus 2. The controller 36 includes an illumination luminance distribution control unit 361 and a stage position control unit 362.

The illumination luminance distribution control unit 361 controls, based on the luminance distribution information created by the illumination luminance distribution estimation unit 341, the luminance distribution of the light to be emitted in the imaging range, by outputting a field stop control signal for adjusting the aperture size of the epi-illumination field stop 214 or the transmission field stop 224.

Figure 5:
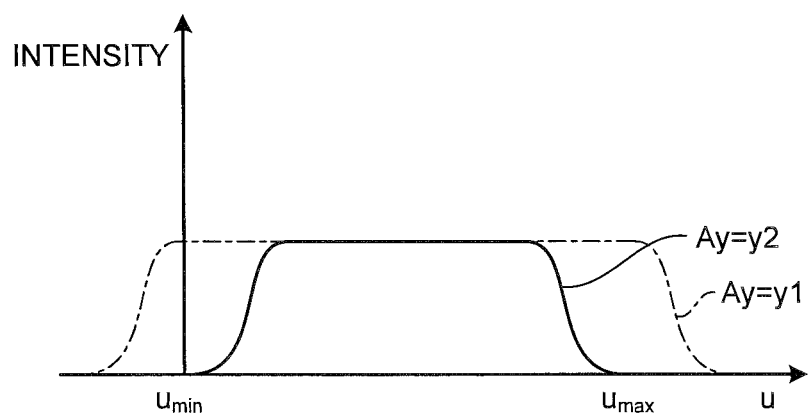
FIG. 5 is a schematic diagram of a luminance profile of light to be emitted in an imaging range.

FIG. 5 is a schematic diagram of a luminance profile of the irradiation light on the imaging range V. FIG. 5 indicates the luminance profile in a u direction, which passes through an optical axis L0 of the objective lens 205. In a typical microscope apparatus, as illustrated in FIG. 3, the positions of the aperture members 214a and 214b (Ay=y1 in FIG. 3, for example) are determined such that the image of the aperture end portion 214d of the epi-illumination field stop 214 (or the transmission field stop 224) does not overlap with the imaging range V. Alternatively, the configuration may be, in some cases, such that the aperture end portion 214d is arranged so as to be adjacent to the imaging range V. In this case, as illustrated in FIG. 5, the irradiation light keeps sufficient intensity even at an end portion (u=$u_{min}$, $u_{max}$) of the imaging range V.

On the other hand, in the first embodiment, as illustrated in FIG. 4, the positions of the aperture members 214a and 214b (Ay=y2 in FIG. 4, for example) are determined such that the image of the aperture end portion 214d of the epi-illumination field stop 214 (or the transmission field stop 224) overlaps with a peripheral area within the imaging range V. With this configuration, the irradiation light attenuates gradually from the inside to the outside in the peripheral area. It is desirable that intensity of the irradiation light is zero at an end portion of the imaging range V.

In other words, in the first embodiment, the epi-illumination field stop 214 or the transmission field stop 224, and the illumination luminance distribution control unit 361 for controlling the aperture sizes of these field stops constitute an illumination control unit that controls luminance distribution of the light to be emitted in the imaging range V.

The stage position control unit 362 is an imaging range movement control unit configured to move the imaging range V by moving the specimen stage 202 on which the specimen SP is placed, relative to the objective lens 205. Based on the stage movement amount calculated by the positioning unit 342, the stage position control unit 362 outputs a stage control signal for operating the stage position changing unit 209, thereby controlling the position of the specimen stage 202 in each imaging timing of the imaging unit 200.

In the first embodiment, the computing unit 34 and the controller 36 may be configured by dedicated hardware, or configured by reading a specified program into hardware such as a CPU. In the latter case, the storage unit 33 further stores a control program for controlling operation of each of the microscope apparatus 2 and the control apparatus 3, an image processing program for causing the computing unit 34 to execute various types of calculation processing including image processing, and various types of parameters and setting information used during execution of these programs.

Figure 6:
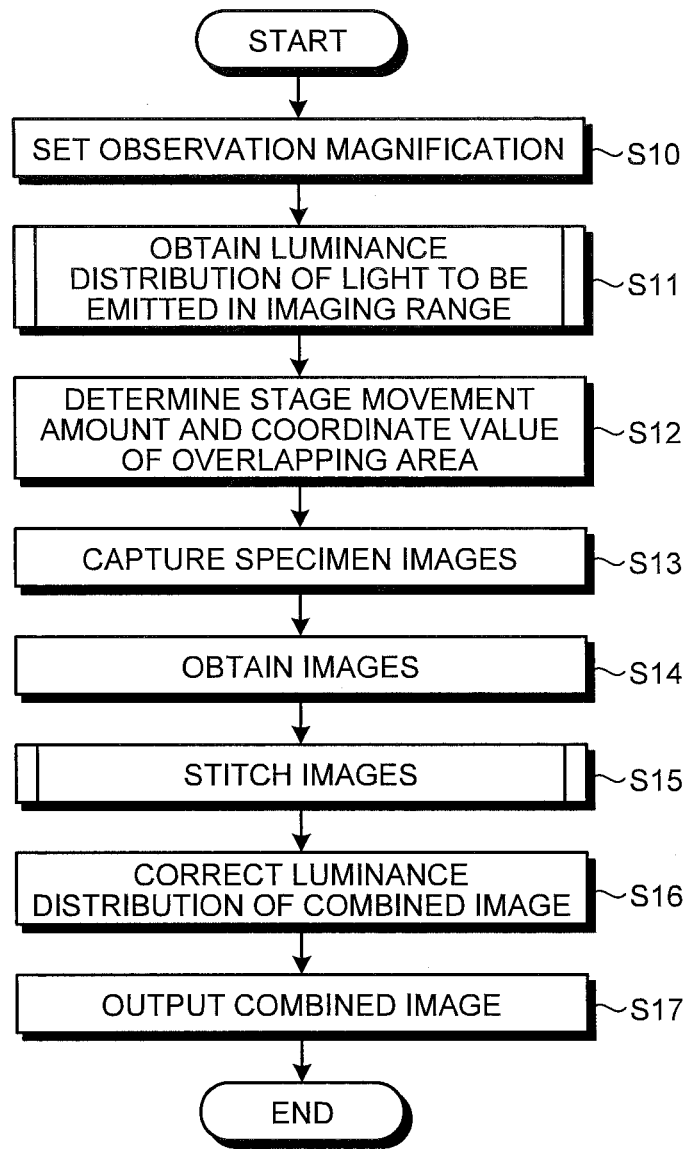
FIG. 6 is a flowchart of operation of the microscope system illustrated in FIG. 1.

Next, operation of the microscope system 1 will be described. FIG. 6 is a flowchart of operation of the microscope system 1. Hereinafter, the following description includes a case in which excitation light is emitted onto a fluorescent-stained specimen SP via the epi-illumination optical system and then an fluorescence image (fluorescence observation image) generated from the specimen SP is obtained.

First, in step S10, the microscope system 1 sets observation magnification for the time of observation of the specimen SP. Specifically, the revolver 230 is rotated, and the objective lens 205 with desired magnification is arranged at a position facing the specimen stage 202.

Figure 7:
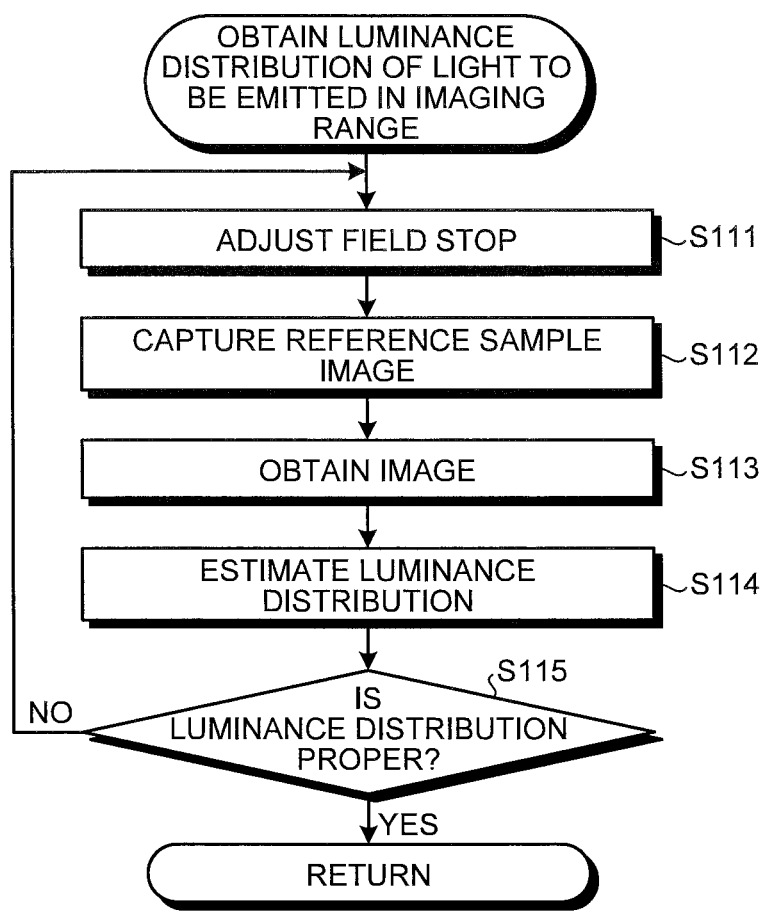
FIG. 7 is a flowchart of acquisition processing of luminance distribution of the light to be emitted in the imaging range.

In subsequent step S11, the microscope system 1 obtains luminance distribution of the light (excitation light) to be emitted in the imaging range of the imaging unit 200. FIG. 7 is a flowchart of acquisition processing of the luminance distribution of the light to be emitted in the imaging range. In step S11, a fluorescent specimen that can generate fluorescence uniformly corresponding to the excitation light intensity is placed, as a reference sample, on the specimen stage 202 of the microscope apparatus 2

In step S111 of FIG. 7, the illumination luminance distribution control unit 361 outputs the field stop control signal so as to adjust the aperture size (positions of the aperture members 214a and 214b) of the epi-illumination field stop 214. At a start of adjustment of the epi-illumination field stop 214, the aperture size is set to its maximum value as initial setting.

In subsequent step S112, the controller 36 causes the imaging unit 200 to capture an image of the reference sample placed on the specimen stage 202.

In step S113, the computing unit 34 obtains an image of the reference sample based on the image data output from the imaging unit 200.

In step S114, the illumination luminance distribution estimation unit 341 estimates, based on a luminance value of each of the pixels constituting the image of the reference sample, luminance distribution of the excitation light emitted in the imaging range and creates luminance distribution information. At this time, this estimation is performed based on a correlation between excitation light intensity and fluorescence intensity.

In step S115, the illumination luminance distribution control unit 361 determines, based on the luminance information created by the illumination luminance distribution estimation unit 341, whether the luminance distribution of the excitation light emitted in the imaging range is proper. Alternatively, the determination may be performed by a user with reference to the image of the reference sample.

Figure 8:
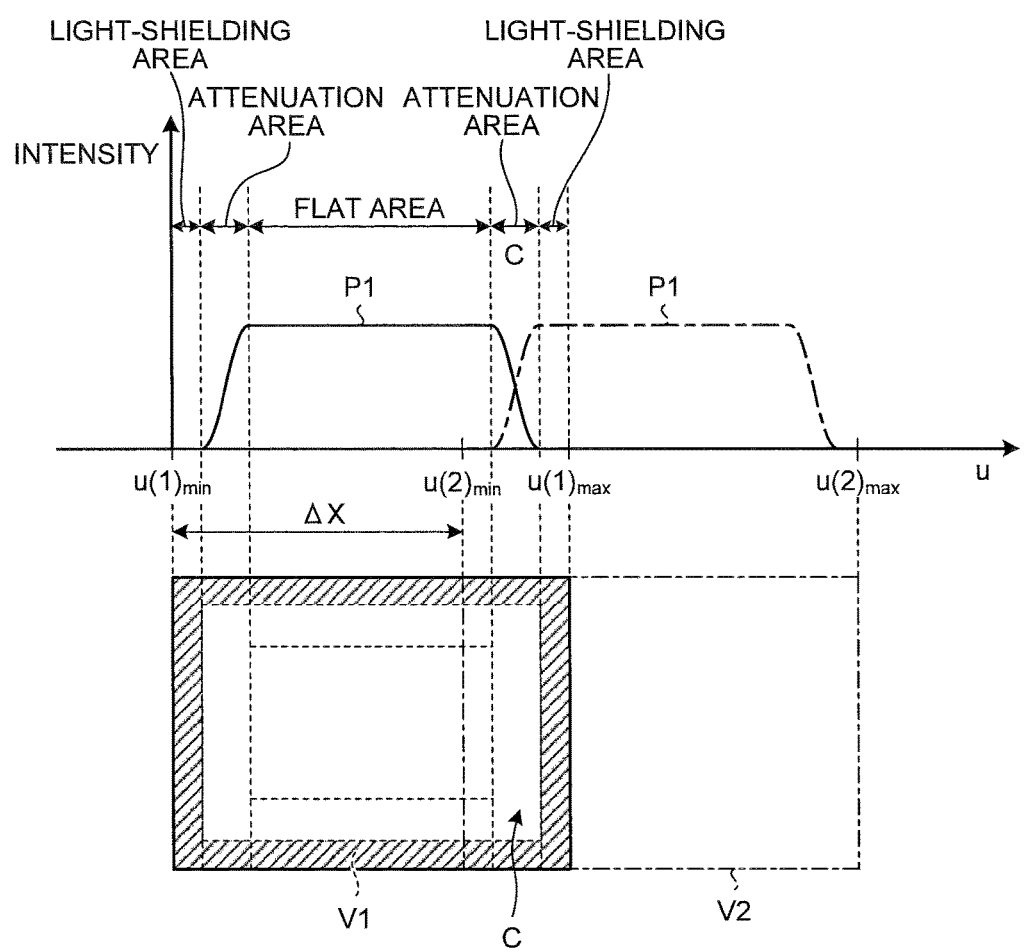
FIG. 8 is a schematic diagram of exemplary desirable luminance distribution of the light to be emitted in the imaging range.

FIG. 8 is a schematic diagram of exemplary desirable luminance distribution of the light (excitation light) to be emitted in the imaging range. A luminance profile P1 illustrated in FIG. 8 indicates a profile of the excitation light to be emitted in an imaging range V1 in the u direction $(u(1)_{min} \leq u \leq u(1)_{max})$.

As illustrated in FIG. 8, the luminance distribution of the excitation light is determined as proper in a case where the distribution attenuates from the inside to the outside in the peripheral area within the imaging range V1 and the intensity becomes zero at the end portion $(u=u(1)_{min}, u(1)_{max})$ or on the inside of the end portion. Hereinafter, in the imaging range V1, a central area in which the excitation light intensity is generally constant is referred to as a flat area and the area in which the intensity is zero is referred to as a light-shielding area. The peripheral area that attenuates the light is also referred to as an attenuation area. In FIG. 8, the light-shielding area of the imaging range V1 is indicated with hatching patterns. Alternatively, it is possible to control an attenuation rate in the attenuation area such that the excitation light intensity becomes zero at the end portion of the imaging range V1. In this case, no light-shielding area is generated.

When the luminance distribution is proper, (Yes in step S115), the processing returns to a main routine. On the other hand, when the luminance distribution is not proper (No in step S115), the processing returns to step S111. In this case, in the subsequent step S111, based on the luminance distribution estimated in step S114, the illumination luminance distribution control unit 361 adjusts the epi-illumination field stop 214 so as to shift the luminance distribution in a proper direction.

In step S12 following step S11, based on the final luminance distribution obtained in step S11, the positioning unit 342 determines the stage movement amount per imaging and a coordinate value of the overlapping area, namely, the overlap width used for stitching images having imaging ranges adjacent to each other.

As illustrated in FIG. 8, the stage movement amount $\Delta X$ in the X direction of the specimen stage 202 that corresponds to the u direction corresponds to a distance from an end of the imaging range V1 $(u=u(1)_{min}$ or $u(1)_{max})$ to an end of an adjacent imaging range V2 $(u=u(2)_{min}$ or $u(2)_{max})$. The stage movement amount $\Delta X$ is determined such that the attenuation areas of the luminance profile P1 overlap with each other between the adjacent imaging ranges V1 and V2. More specifically, the stage movement amount $\Delta X$ is determined, based on the luminance profile P1, such that the accumulated light quantity of the excitation light in an area C overlapping in the imaging ranges V1 and V2 becomes substantially equivalent to the intensity in the flat area.

The positioning unit 342 determines an area on the image that corresponds to the area C overlapping in the imaging ranges V1 and V2 as the overlapping area, and obtains the coordinate value of the overlapping area on the coordinate system on the image.

Similarly, the positioning unit 342 determines the stage movement amount and the coordinate value of the overlapping area, in the Y direction.

In step S13, the microscope system 1 sequentially captures images of the specimen SP that is an object of observation placed on the specimen stage 202 while changing the imaging range. In other words, imaging is performed by applying the excitation light having the luminance distribution obtained in step S11 to the specimen SP, thereafter, the specimen stage 202 is moved by the stage movement amount determined in step S12. The operation sequence is repeated until imaging of the entire specimen SP is completed. With this sequence, image data of different imaging ranges are sequentially output from the imaging unit 200.

At this time, the luminance distribution of the excitation light attenuates at a peripheral area of the imaging range. Accordingly, the accumulated light quantity generated by a plurality of times of emission of the excitation light onto the peripheral area is substantially the same as the light quantity emitted on the flat area. That is, the accumulated light quantity of the excitation light emitted onto the specimen SP is substantially constant on entire areas regardless of the position.

Note that in order to suppress degradation of the specimen SP, it is desirable to protect the specimen SP from light except for the time of imaging (exposure).

In step S14, the computing unit 34 sequentially obtains images with different imaging ranges based on the image data output from the imaging unit 200. At this time, the computing unit 34 obtains, from the position detection unit 236 (refer to FIG. 2), the image data and position information of the specimen stage 202 at the time of imaging of each of the images.

Figure 9:
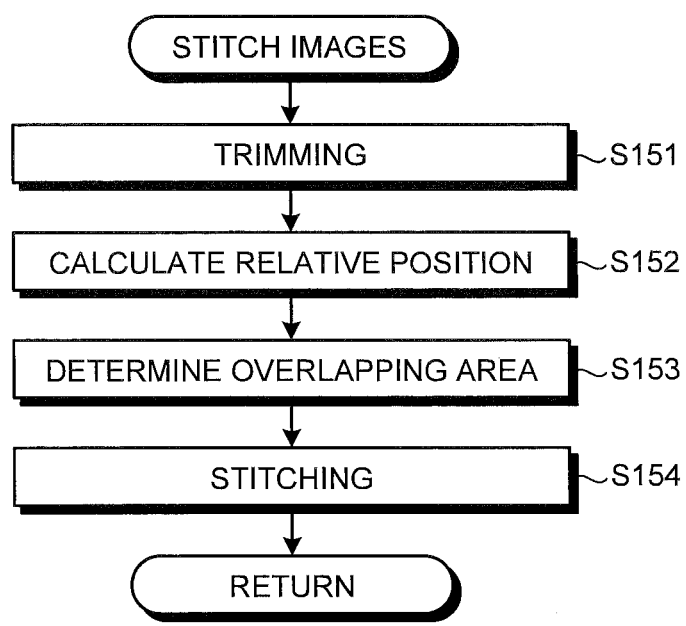
FIG. 9 is a flowchart of image stitching processing according to the first embodiment of the present invention.

In step S15, based on the coordinate value of the overlapping area determined in step S12, the image combining unit 343 stitches the plurality of images input sequentially. FIG. 9 is a flowchart of image stitching processing. FIG. 10 is a schematic diagram for explaining the image stitching processing in which images M1 and M2 whose imaging ranges are adjacent in the u direction are stitched together.

First in step S151, the trimming unit 343a trims an area, namely, cuts out an area, from the images sequentially input, so as to be used for combining. Specifically, as illustrated in (a) of FIG. 10, the images M1 and M2 are trimmed to leave the imaging areas corresponding to the flat area and the attenuation area (that is, the image areas m1 and m2 that correspond to the light-shielding area are removed). With this procedure, trimmed images M1' and M2' are created. When the luminance distribution has been controlled so as to set the excitation light intensity at the end portions ($u=u_{min}$, $u_{max}$) of the imaging range to zero, no light-shielding area is generated on the obtained image. In this case, step S151 may be omitted.

In the subsequent step S152, based on the position information of the specimen stage 202 obtained from the position detection unit 236, the combining unit 343b calculates a relative position of the trimmed image M2' with respect to the trimmed image M1'.

In step S153, based on the coordinate value of the overlapping area calculated by the positioning unit 342, the combining unit 343b determines an overlapping area to be overlapping on the images M1' and M2'.

Furthermore in step S154, as illustrated in (b) of FIG. 10, the combining unit 343b stitches the images M1' and M2' such that the images overlap with each other in the overlapping area determined in step S153.

Figure 11:
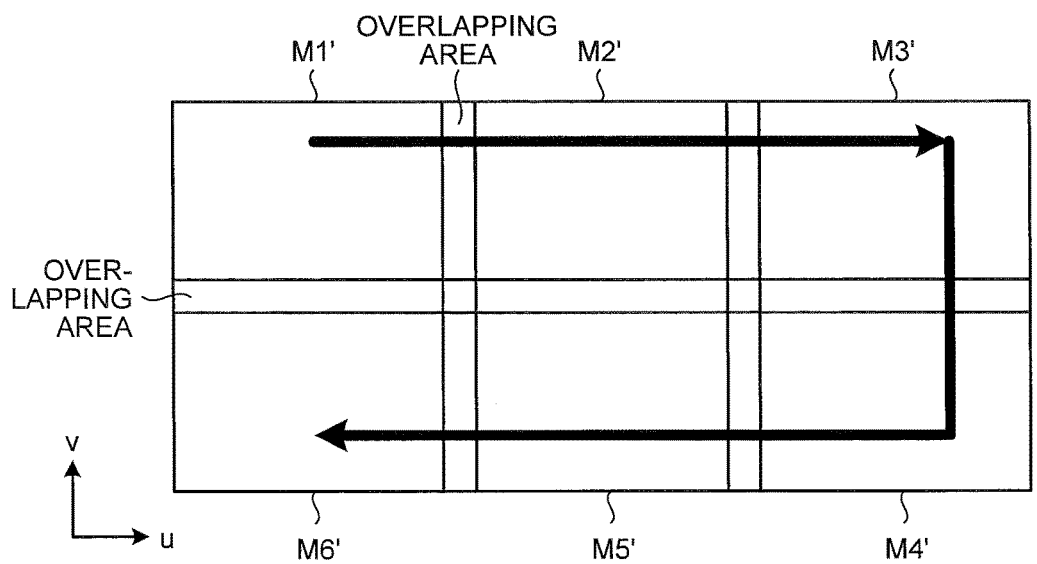
FIG. 11 is a schematic diagram for explaining the image stitching in 3×2 matrix.

The combining unit 343b sequentially performs this stitching processing each time image data is input from the imaging unit 200, thereby creating a combined image with a wide field. For example, in a case where the imaging range has a 3×2 matrix form as illustrated in FIG. 11, imaging is performed, as illustrated with the arrows in FIG. 11, so as to move in a substantially U-shape on the imaging range, and stitching processing is performed in an order of image acquisition. Specifically, after the trimmed images M1' to M3' are sequentially stitched in the u direction, the trimmed image M4' is stitched in a −v direction, and then, the trimmed images M5' and M6' are sequentially stitched in a −u direction. Thereafter, the processing returns to the main routine.

Figure 12:
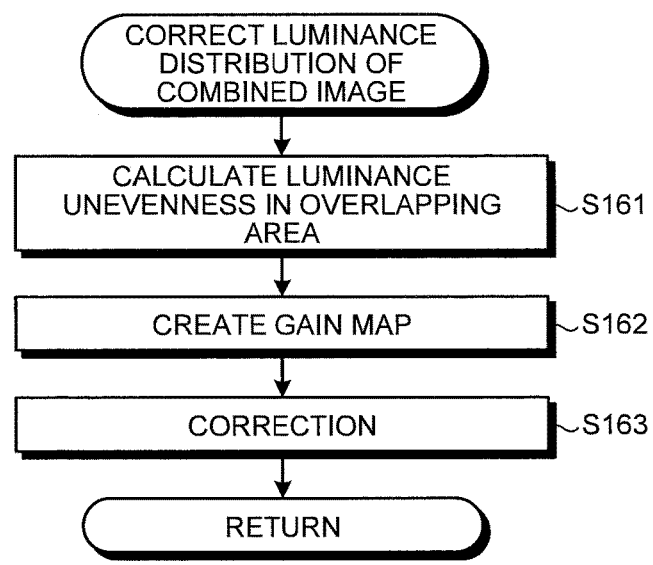
FIG. 12 is a flowchart of correction processing of luminance distribution in a combined image.
Figure 13:
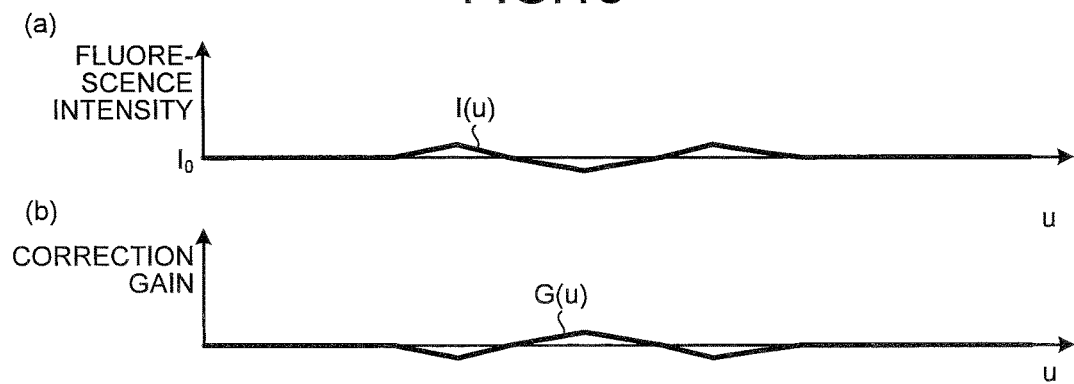
FIG. 13 is a schematic diagram for explaining the correction processing of the luminance distribution in the combined image.

In step S16 following step S15, the image luminance distribution correction unit 344 corrects the luminance distribution of the combined image created in step S15. FIG. 12 is a flowchart of correction processing of the luminance distribution in the combined image. FIG. 13 is a schematic diagram for explaining the correction processing of the luminance distribution in the combined image.

First, in step S161, the luminance unevenness calculation unit 344a obtains, from the illumination luminance distribution estimation unit 341, the luminance distribution of fluorescence generated at the time of imaging the reference sample (refer to step S11). Then, based on the obtained luminance distribution, the luminance unevenness calculation unit 344a calculates the luminance unevenness generated when the overlapping areas are overlapped between the adjacent images. As illustrated in (a) of FIG. 13, the difference of fluorescence intensity I(u) with respect to fluorescence intensity $I_0$ is determined as the luminance unevenness in the u direction.

In the following step S162, based on the fluorescence intensity calculated in step S161, the correction gain calculation unit 344b calculates a correction gain G(u) for each of points in the overlapping area and creates a gain map (refer to (b) of FIG. 13). The image luminance distribution correction unit 344 may incorporate the luminance distribution information at a time point when the illumination luminance distribution estimation unit 341 has estimated the luminance distribution of the excitation light (refer to step S11), and may create and retain the gain map.

In step S163, the correction unit 344c corrects the luminance unevenness in the overlapping area of the combined image by using the gain map created in step S162. Thereafter, the processing returns to the main routine.

In step S17 following step S16, the computing unit 34 outputs the created combined image and displays it on an external apparatus such as a display apparatus, and stores the combined image in the storage unit 33. Thereafter, operation of the microscope system 1 is finished.

As described above, according to the first embodiment, the luminance distribution of the irradiation light is controlled such that the irradiation light attenuates in the peripheral area within the imaging range. In addition, imaging is performed while the specimen stage 202 is moved so as to cause the adjacent imaging ranges to overlap with each other in the peripheral area. With this configuration, it is possible to allow the accumulated light quantity of the irradiation light on the peripheral area to be substantially the same as that of the central portion of the imaging range. In other words, the accumulated light quantity of the light emitted on the specimen SP can be generally equalized. Accordingly, it is possible to suppress local degradation of the specimen SP due to exposure to light.

Moreover, according to the first embodiment, the aperture size is adjusted such that the image of the aperture end portion of the epi-illumination field stop 214 overlaps with the imaging range. With this configuration, the luminance distribution of the irradiation light is controlled accordingly, and it is possible to achieve light irradiation suitable to the imaging range.

The above-described first embodiment has described a case where fluorescence observation is performed on the microscope apparatus 2. Alternatively, the above-described first embodiment is applicable also to other microscopy methods such as transmission observation, phase difference observation, and differential interference observation performed on the microscope apparatus 2. In these cases, it is merely required to control the aperture size of the epi-illumination field stop 214 or the transmission field stop 224, according to the microscopy methods.

Moreover, in the above-described first embodiment, the imaging field of view is moved by moving the specimen stage 202 on which the specimen SP is placed while fixing the position of the observation optical system including the objective lens 205. Alternatively, it is possible to move the observation optical system while fixing the specimen SP. Alternatively, it is possible to move both of the specimen SP and the observation optical system relative to each other.

Modification Example 1-1

Next, Modification Example 1-1 of the first embodiment of the present invention will be described.

Figure 14:
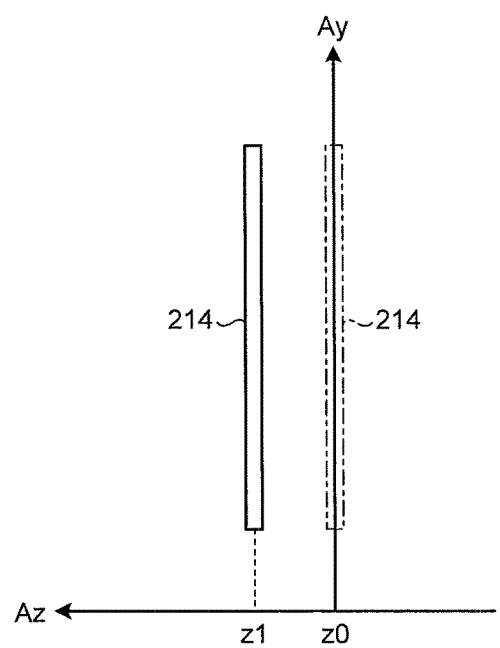
FIG. 14 is a schematic diagram of arrangement of a field stop in Modification Example 1-1 of the first embodiment of the present invention.
Figure 15:
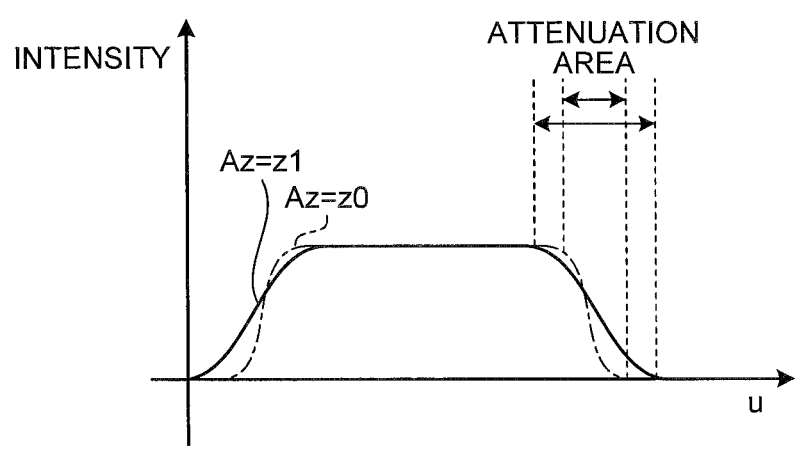
FIG. 15 is a graph of a luminance profile of irradiation light corresponding to the arrangement of the field stop illustrated in FIG. 14.

FIG. 14 is a schematic diagram for explaining arrangement of the field stop in Modification Example 1-1. FIG. 15 a graph of a luminance profile of the irradiation light corresponding to the arrangement illustrated in FIG. 14. In Modification Example 1-1, the aperture size of the field stop is adjusted, and the position of the field stop in an optical axis direction is adjusted. With this configuration, the luminance distribution of the irradiation light is controlled.

As illustrated in FIG. 14, the epi-illumination field stop 214 is normally arranged at a position Az=z0 conjugated with the specimen SP. In this case, as illustrated in a broken line in FIG. 15, the rising portion of the luminance distribution of the irradiation light looks relatively sharp, making clear the contrast at a boundary of an exposure area of the irradiation light.

On the other hand, in Modification Example 1-1, the epi-illumination field stop 214 is arranged at a position displaced from the conjugated position Az=z0 (for example, at Az=z1). With this arrangement, as illustrated in a solid line in FIG. 15, the rising portion of the irradiation light intensity in the peripheral area looks more gentle, making the attenuation area broader than the case of Az=z0. In other words, the overlapping area within adjacent imaging ranges become broader, making it possible to improve positioning accuracy at the time of image stitching.

As described above, according to Modification Example 1-1, by adjusting the position of the epi-illumination field stop 214 in the Az direction, it is possible to control each of a width of the attenuation area and the attenuation rate of the luminance in the attenuation area to be a desirable value.

In the transmitted-light illumination optical system, by adjusting the position of the transmission field stop 224 in an optical axis direction, it is possible to control the luminance distribution of the irradiation light.

Modification Example 1-2

Next, Modification Example 1-2 of the first embodiment of the present invention will be described.

In the above-described first embodiment, the epi-illumination field stop 214 and the transmission field stop 224 are configured with the aperture members 214a and 214b formed of a light-shielding member (refer to FIGS. 3 and 4). Alternatively, the aperture members 214a and 214b may be formed of a member in which transmittance is continuously changed (reduced) as the distance from the aperture end portion increases. Specifically, metal is deposited on a transparent member such as glass so as to form a thin film. By adjusting the thickness of the film at this time, it is possible to change transmittance.

In this case, it is possible to gradually attenuate the irradiation light on the peripheral area of the imaging range without moving the aperture members 214a and 214b in the optical axis Az direction. Moreover, by designing appropriately the level of transmittance and the rate of change of the transmittance on the aperture members 214a and 214b, it is possible to achieve luminance distribution of the irradiation light corresponding to the types of microscopy methods and fluorescence.

Modification Example 1-3

Next, Modification Example 1-3 of the first embodiment of the present invention will be described.

In the above-described first embodiment, various control information (field stop position information, stage movement amount, and coordinate value of the overlapping area) is obtained based on a result of imaging the reference sample. Alternatively, it is possible to obtain the control information, or the like, by a specimen to be observed, as long as the specimen generates uniform fluorescence. In this case, in order to prevent the area to be observed within the specimen from being degraded, it is desirable that areas other than the area to be observed are imaged.

Second Embodiment

Next, a second embodiment of the present invention will be described.

Figure 16:
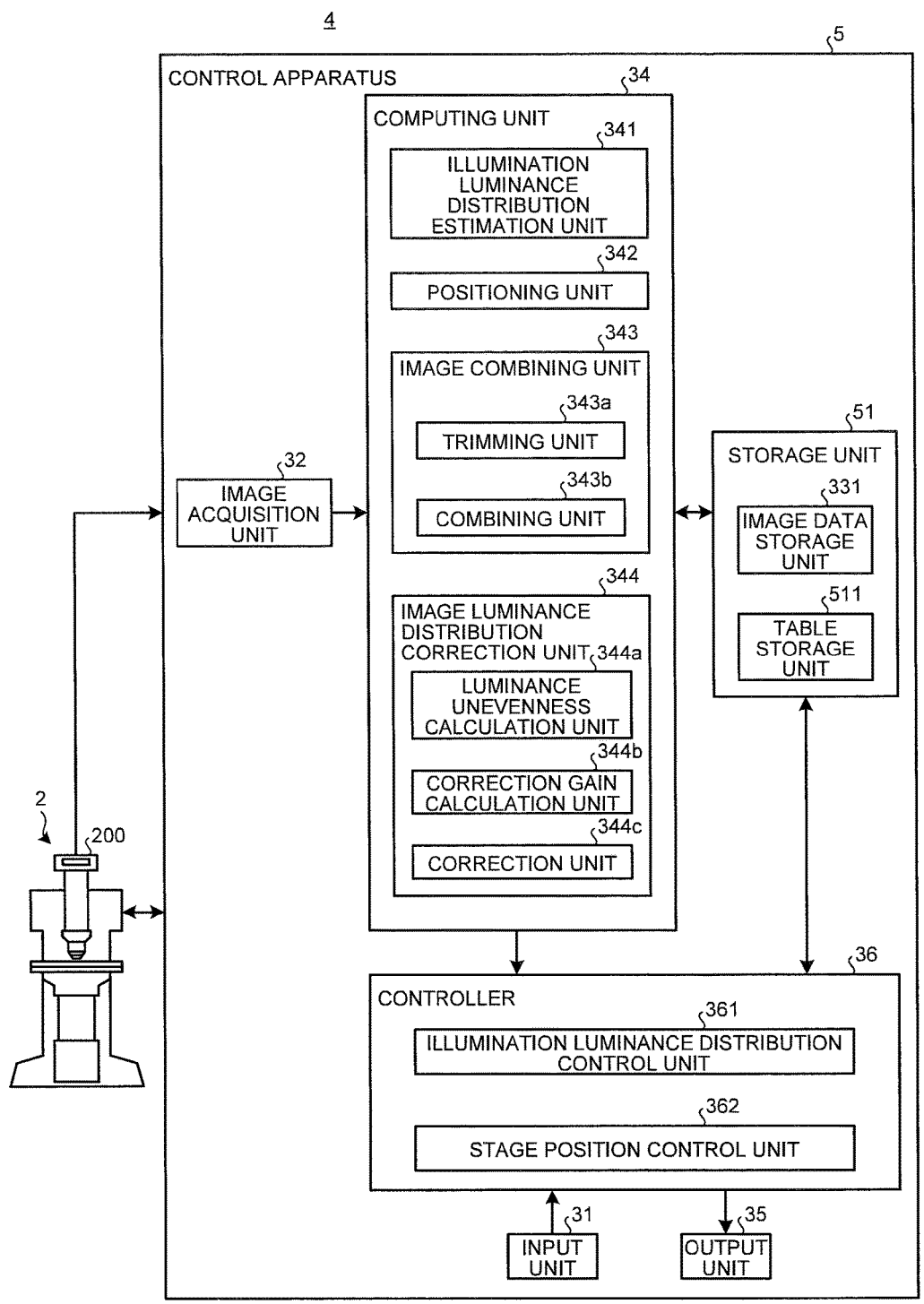
FIG. 16 is a configuration diagram of a microscope system according to a second embodiment of the present invention.

FIG. 16 is a configuration diagram of a microscope system according to the second embodiment of the present invention. As illustrated in FIG. 16, a microscope system 4 according to the second embodiment includes a microscope apparatus 2 and a control apparatus 5. Among these, configuration and operation of the microscope apparatus 2 are similar to those in the first embodiment.

In contrast to the control apparatus 3 in FIG. 1, the control apparatus 5 includes a storage unit 51 having a table storage unit 511. Configurations and operation of each of the units other than the storage unit 51 in the control apparatus 5 are similar to those in the first embodiment.

The table storage unit 511 stores a luminance distribution table. The luminance distribution table stores luminance distribution of the irradiation light corresponding to the observation magnification of the microscope apparatus 2, and control information on the field stop to achieve the luminance distribution, namely, the position information of the aperture members 214a and 214b in the Ax, Ay, and Az directions. It is also possible to create this type of luminance distribution table based on a reference sample prepared by imaging on the microscope apparatus 2 beforehand, or based on a result of measurement or simulation that is performed separately.

Figure 17:
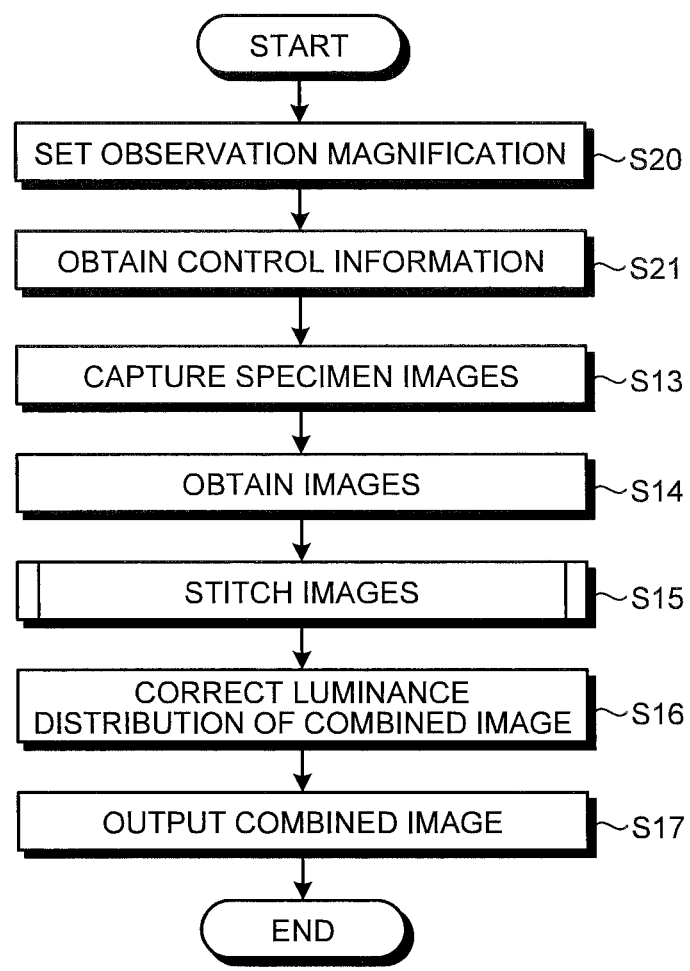
FIG. 17 is a flowchart of operation of the microscope system illustrated in FIG. 16.

Next, operation of the microscope system 4 will be described. FIG. 17 is a flowchart of operation of the microscope system 4.

First, in step S20, observation magnification at a time of observation of the specimen SP is set. Specifically, the revolver 230 is rotated so as to arrange the objective lens 205 with desired magnification at a position facing the specimen stage 202. With this arrangement, an output value on an encoder provided on the revolver 230 is input into the control apparatus 5. The controller 36 obtains observation magnification on the microscope apparatus 2 based on the output value.

In the subsequent step S21, the controller 36 obtains, from the luminance distribution table, luminance distribution of the irradiation light and control information of the field stop corresponding to the observation magnification on the microscope apparatus 2. Based on the luminance distribution of the irradiation light obtained by the controller 36, the positioning unit 342 calculates the stage movement amount per imaging and the coordinate value of the overlapping area on the adjacent images.

Operations in the subsequent steps S13 to S17 are similar to those in the first embodiment.

As described above, according to the second embodiment, control information on the field stop corresponding to the observation magnification is obtained from the luminance distribution table prepared beforehand. Accordingly, there is no need to perform operation including adjustment of the field stop position by imaging the reference sample beforehand. With this configuration, it is possible to obtain a wide-field image of the specimen SP in a shorter time.

In the above-described second embodiment, calculation of the stage movement amount and the coordinate value of the overlapping area is performed based on the luminance distribution of the irradiation light obtained from the luminance distribution table. Alternatively, it is possible to incorporate the stage movement amount and the coordinate value of the overlapping area in association with the observation magnification and then stored as a table.

Third Embodiment

Next, a third embodiment of the present invention will be described.

Figure 18:
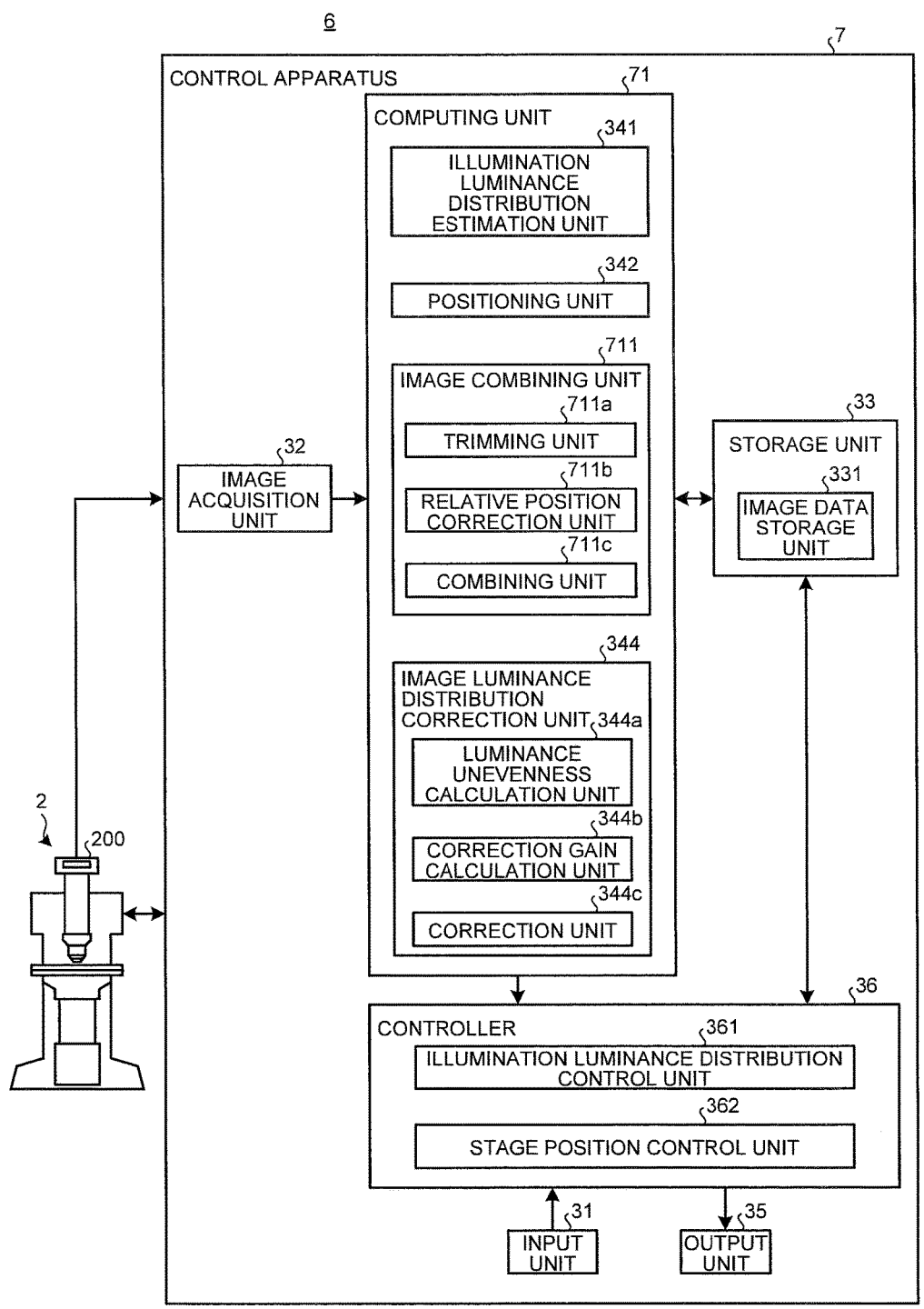
FIG. 18 is a configuration diagram of a microscope system according to a third embodiment of the present invention.

FIG. 18 is a configuration diagram of a microscope system according to the third embodiment of the present invention. As illustrated in FIG. 18, a microscope system 6 according to the third embodiment includes a microscope apparatus 2 and a control apparatus 7. Among these, configuration and operation of the microscope apparatus 2 are similar to the case in the first embodiment.

In contrast to the control apparatus 3 in FIG. 1, the control apparatus 7 includes a computing unit 71 having an image combining unit 711 instead of the image combining unit 343. Configurations and operation of each of the units in the control apparatus 7 other than the image combining unit 711 are similar to those in the first embodiment.

The image combining unit 711 includes a trimming unit 711*a*, a relative position correction unit 711*b*, and a combining unit 711*c*. The trimming unit 711*a* trims, from each of the images acquired via the image acquisition unit 32, an area to be used for image combining. The relative position correction unit 711*b* corrects relative positions of the images based on a feature in the overlapping area on adjacent images. The combining unit 711*c* stitches the images with each other whose positions have been corrected by the relative position correction unit 711*b*. Operation of the trimming unit 711*a* is similar to the operation of the trimming unit 343*a* illustrated in FIG. 1.

In the microscope system 6, similarly in the first embodiment, the stage movement amount and the coordinate value of the overlapping area on the adjacent images are calculated based on the luminance distribution of the irradiation light, and imaging is performed while the specimen stage 202 is moved according to the stage movement amount. When the imaging with this method is executed consecutively, however, there are cases where misalignment occurs on the specimen stage 202 due to an influence of backlash, or the like. In this case, if image stitching is performed uniformly by using the coordinate value of the overlapping area calculated based on the luminance distribution of the irradiation light, stitching accuracy might be lowered. To improve this, in the third embodiment, a feature area is extracted from the overlapping area of the obtained image. Then, based on the extracted feature area, individual alignment is executed so as to improve accuracy in stitching images with each other.

Figure 19:
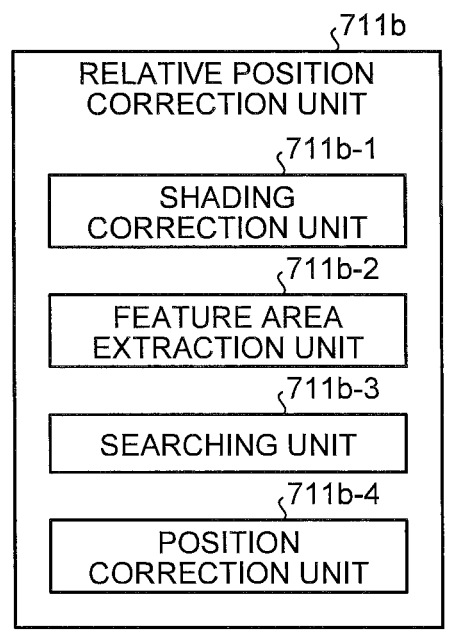
FIG. 19 is a block diagram of a configuration of a relative position correction unit illustrated in FIG. 18.

FIG. 19 is a block diagram of a configuration of the relative position correction unit 711*b*. As illustrated in FIG. 19, the relative position correction unit 711*b* includes a shading correction unit 711*b*-1, a feature area extraction unit 711*b*-2, a searching unit 711*b*-3, and a position correction unit 711*b*-4. The shading correction unit 711*b*-1 performs shading correction for the overlapping area of each of the images. The feature area extraction unit 711*b*-2 extracts a feature area from the overlapping area on which shading correction has been performed. Based on the extracted feature area, the searching unit 711*b*-3 searches an area that has a high correlation with each other in the overlapping areas. Based on a result of the searching, the position correction unit 711*b*-4 corrects relative positions of adjacent images.

Next, operation of the microscope system 6 will be described.

Figure 20:
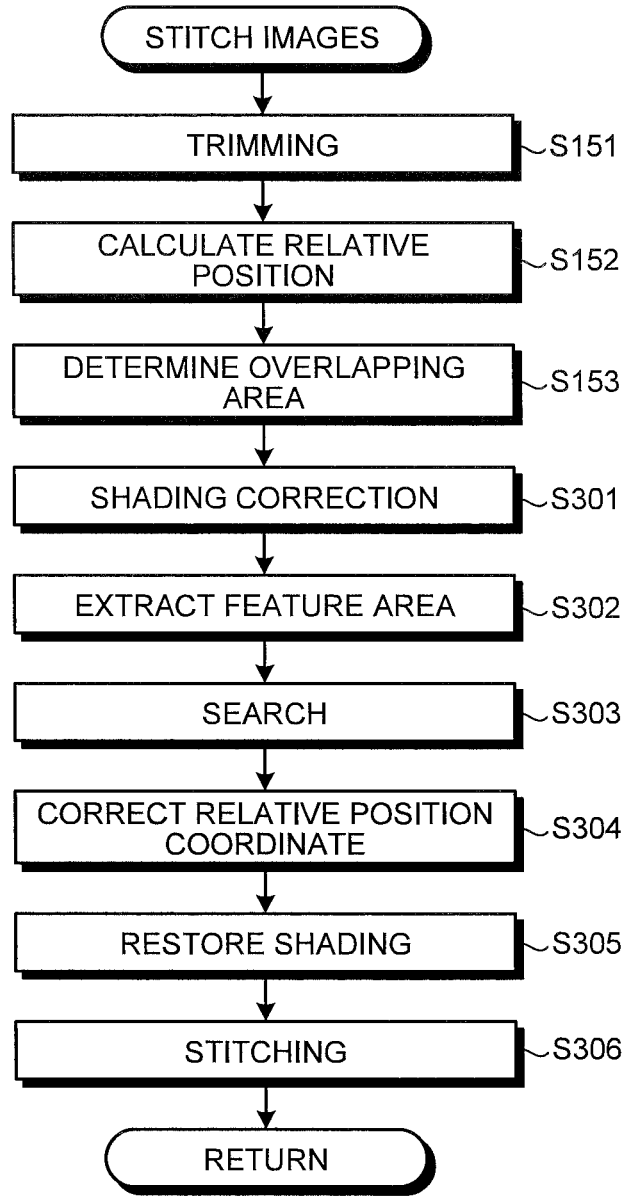
FIG. 20 is a flowchart of image stitching processing in the third embodiment of the present invention.

Operation of the microscope system 6 is generally similar to the operation illustrated in FIG. 6 except for image stitching processing in step S15, which differs from the case in the first embodiment. FIG. 20 is a flowchart of image stitching processing in the third embodiment. Processing in the subsequent steps S151 to S153 is similar to the operation in the first embodiment (refer to FIG. 9).

Figure 21:
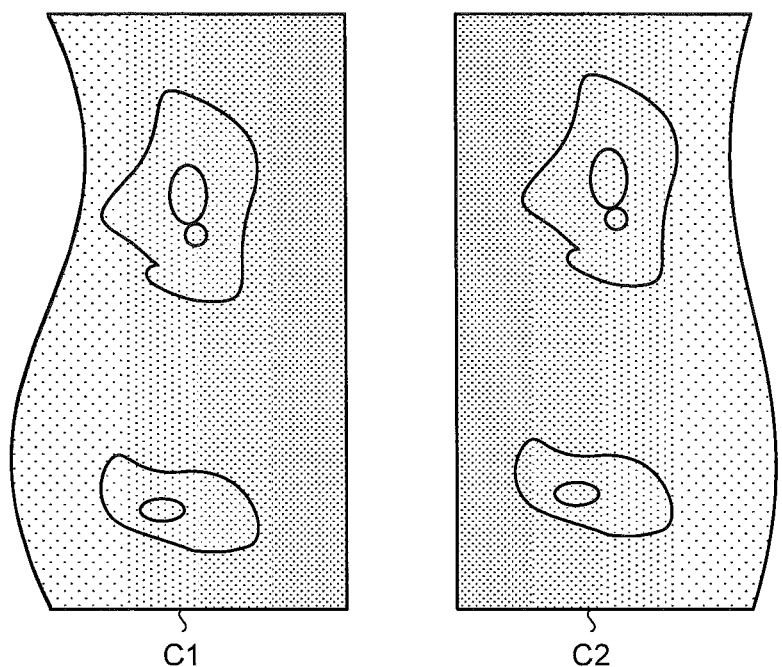
FIG. 21 is a schematic diagram of a part of an overlapping area of two adjacent images.
Figure 22:
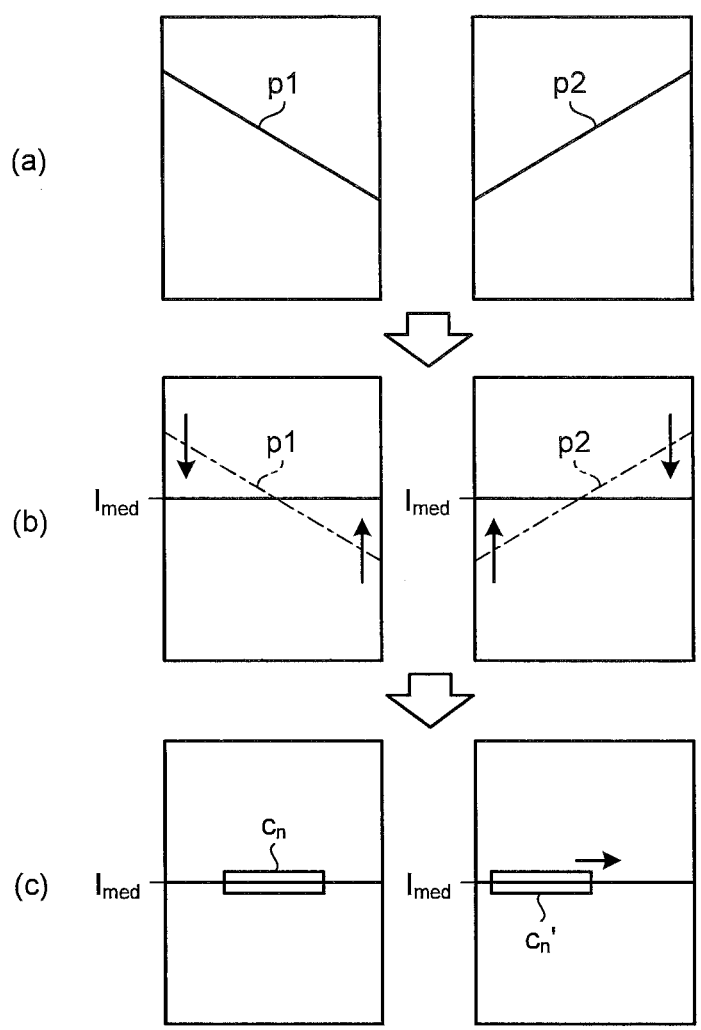
FIG. 22 is a schematic diagram of shading correction processing for the overlapping area illustrated in FIG. 21.

In step S301 following step S153, the shading correction unit 711*b*-1 performs shading correction for the overlapping area of each of the images. FIG. 21 is a schematic diagram of a part of an overlapping area of two adjacent images. Among these, an overlapping area C1 illustrated in FIG. 21 is an image area that corresponds to the area C on a right end of the imaging range V1 illustrated in FIG. 8. An overlapping area C2 is an image area that corresponds to the area C on a left end of the imaging range V2. FIG. 22 is a schematic diagram of shading correction processing for the overlapping area.

As shown in the luminance profile P1 in FIG. 8, the light to be emitted in each of the imaging ranges V1 and V2 is controlled to attenuate from the inner side toward the edge in the peripheral area. This causes symmetrical shading in the overlapping areas C1 and C2 to be overlapping with each other, making it difficult to perform correlation calculation for both areas. To cope with this, the shading correction unit 711*b*-1 performs shading correction for each of the overlapping areas C1 and C2 so as to normalize luminance.

Specifically, based on the luminance profile P1 of the irradiation light, each of luminance profiles p1 and p2 on each of shading components is obtained in advance corresponding to each of the overlapping areas C1 and C2, as illustrated in (a) of FIG. 22. As illustrated in (b) of FIG. 22, regarding the overlapping area C1, a correction gain is employed in which, with reference to a median $I_{med}$ of the luminance profile p1 of the shading component, the luminance is lowered on the inner side (left side of the figure) of the image, and the luminance is raised on the outer side (right side of the figure) of the image. On the other hand, regarding the overlapping area C2, a correction gain is employed in which, with reference to a median $I_{med}$ of the luminance profile p2 of the shading component, the luminance is lowered on the inner side (right side of the figure) of the image, and the luminance is raised on the outer side (left side of the figure) of the image. As described above, a gain at each of the overlapping areas C1 and C2 is adjusted with reference to the median $I_{med}$ of each of the luminance profiles p1 and p2 of the shading component, making it possible to decrease the ratio of gain increase from the darker portion. This configuration thus can suppress occurrence of noise.

Figure 23:
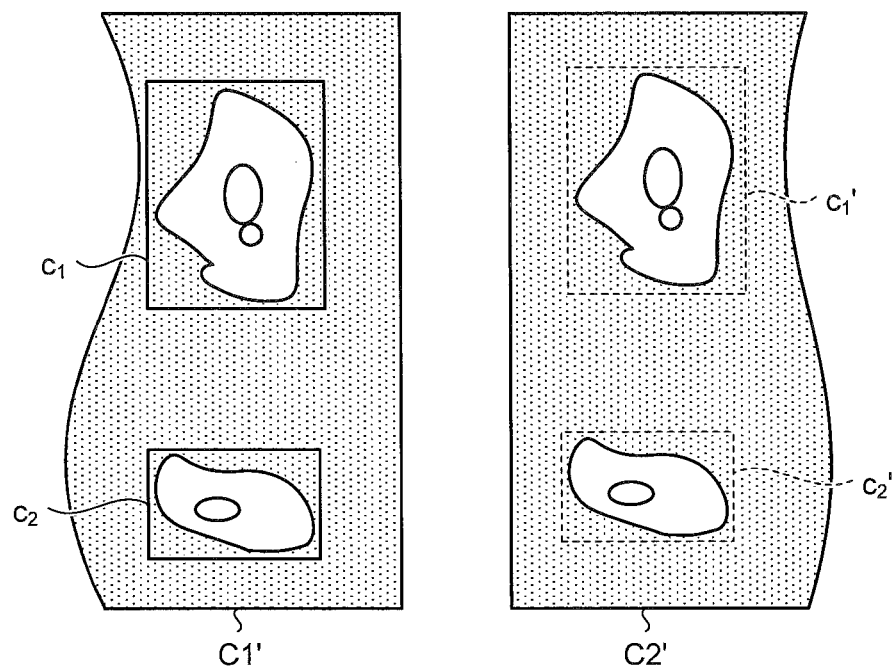
FIG. 23 is a schematic diagram of the overlapping area on which the shading correction has been performed.

In the following step S302, the feature area extraction unit 711$b$-2 extracts a feature area $c_n$ (n=1, 2, . . . ) to be used for alignment, as illustrated in FIG. 23, from any of the overlapping areas C1' and C2' on which shading correction has been performed. FIG. 23 illustrates an example in which two feature areas $c_1$, and $c_2$ are extracted from the overlapping area C1'.

In step S303, based on the feature area $c_n$ extracted from one overlapping area C1', the searching unit 711$b$-3 searches for another overlapping area C2', and then, detects an area $c_n'$ that has high correlation with the feature area $c_n$.

In step S304, the position correction unit 711$b$-4 calculates the amount of misalignment between the overlapping areas C1' and C2', based on a detection result in step S303, as illustrated in (c) of FIG. 22, and then corrects, for the amount of misalignment, a relative position coordinate at the time of stitching each of images including each of the overlapping areas C1 and C2, with each other.

In step S305, the shading correction unit 711$b$-1 restores shading corrected in step S301 for each of the overlapping areas C1 and C2.

In step S306, based on the relative position coordinate corrected in step S304, the combining unit 343$b$ stitches the images including each of the overlapping areas C1 and C2. Thereafter, the processing returns to the main routine (refer to FIG. 6).

As described above, according to the third embodiment, luminance in each of the overlapping areas is normalized by shading correction. Accordingly, it is possible to perform correlation calculation based on the feature area existing in the overlapping area. With this configuration, it is possible to correct misalignment occurring in stitching adjacent images with each other and improve stitching accuracy. In particular, a fluorescence image has a background that is a dark area with very little feature data. Therefore, by determining the feature area extracted from the overlapping area to be a window for the correlation calculation, it is possible to precisely calculate the amount of misalignment between the images.

The image stitching processing in the third embodiment may be applied to the second embodiment.

Modification Example 3-1

Next, Modification Example 3-1 of the third embodiment of the present invention will be described.

In the above-described third embodiment, the correction gain is determined with reference to the median $I_{med}$ of each of the luminance profiles p1 and p2 of the shading component. Alternatively, as illustrated in (a) and (b) of FIG. 24, shading correction may be performed with reference to the maximum value $I_{max}$ of each of the luminance profiles p1 and p2 of the shading component, so as to increase the gain on a low-luminance side.

Figure 24:
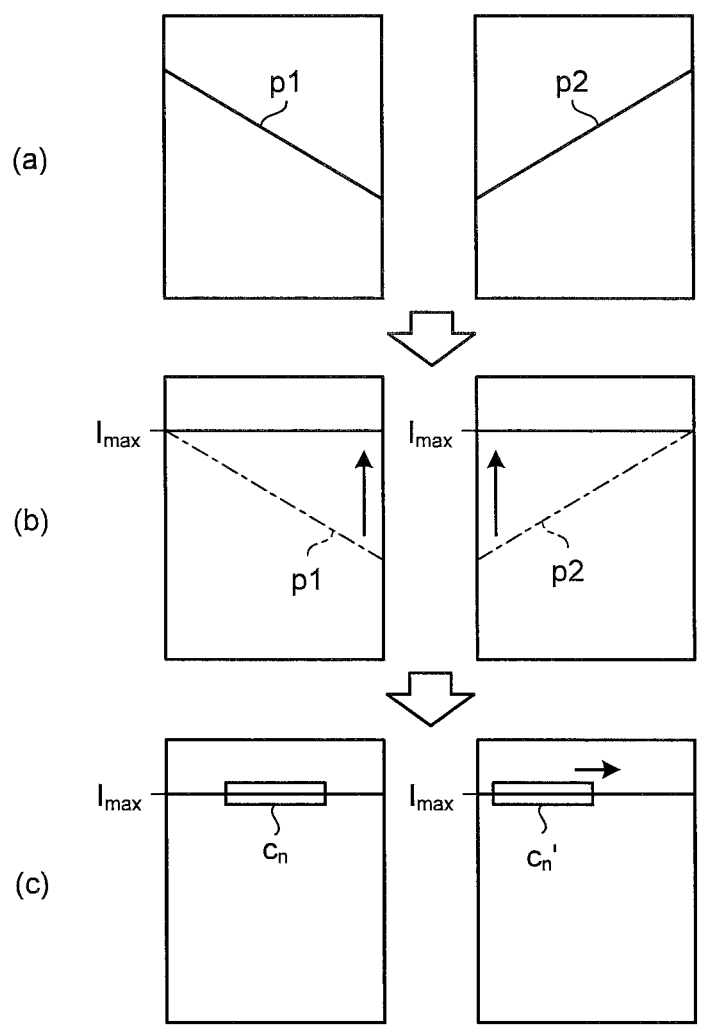
FIG. 24 is a schematic diagram of shading correction processing for the overlapping area in Modification Example 3-1 of the third embodiment of the present invention.

In this case, as illustrated in (c) of FIG. 24, correlation calculation can be executed based on the feature area $c_n$ having sufficient luminance. Accordingly, it is possible to calculate the amount of misalignment between the images more precisely.

The present invention is not limited to a case in which any of the above-described first to third embodiments and their Modification Examples is executed as it is. By combining appropriately a plurality of components disclosed in each of the first to third embodiments and their Modification Examples, it is possible to form a variety of inventions. For example, it is possible to form an invention by removing some components from the entire components illustrated in the first to third embodiments and their Modification Examples. Alternatively, it is possible form the invention by appropriately combining components illustrated in different embodiments.

According to some embodiments, the luminance distribution of the light to be emitted in the imaging range is controlled such that the light attenuates in the peripheral area inside the imaging range. The imaging range is moved such that the peripheral areas overlap with each other in the adjacent imaging ranges. With this configuration, it is possible to set the accumulated light quantity of the light emitted in the peripheral area to be substantially the same as that in another area, and to suppress local degradation of the specimen due to exposure to light.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging apparatus comprising:
    one or more processors comprising hardware, wherein the one or more processors are configured to:
        control an image sensor to image an object within an imaging range to generate image data;
        control a light source to generate light to be emitted in the imaging range;
        control a field stop to adjust luminance distribution of the light such that the light continuously attenuates from an inner side toward an edge in a peripheral area within the imaging range;
        control an actuator to move one or more of a stage on which the object is placed and the image sensor to sequentially move the imaging range relative to the object such that entire peripheral areas where the light attenuates overlap with each other in adjacent imaging ranges; and
        sequentially obtain, from the image sensor, the image data of a plurality of images with different imaging ranges and create a combined image by stitching the plurality of images in such a way that adjacent images of the plurality of images corresponding to the adjacent imaging ranges are stitched together such that image areas corresponding to the entire peripheral areas overlap with each other.

2. The imaging apparatus according to claim 1, comprising:
    the field stop,
    wherein the field stop is provided on an optical path of the light, and
    wherein the optical path extends from the light source to the object.

3. The imaging apparatus according to claim 2,
    wherein the one or more processors are configured to:
        control the field stop to adjust an aperture size of the field stop such that an image of an aperture end portion of the field stop overlaps with a peripheral portion of the imaging range; and
        control the actuator to sequentially move the imaging range according to the aperture size.

4. The imaging apparatus according to claim 2,
wherein the one or more processors are configured to:
control the field stop to move along the optical path; and
control the actuator to sequentially move the imaging range according to a position of the field stop in a direction of the optical path.

5. The imaging apparatus according to claim 3,
wherein the field stop is formed of a member in which transmittance of the light continuously changes as a distance from the aperture end portion increases.

6. The imaging apparatus according to claim 1,
wherein the one or more processors are configured to:
extract a feature area from the image areas of the adjacent images corresponding to the adjacent imaging ranges; and
execute alignment of the adjacent images based on the feature area.

7. The imaging apparatus according to claim 6,
wherein the one or more processors are configured to:
perform shading correction on the image areas of the adjacent images corresponding to the adjacent imaging ranges; and
execute the alignment based on the image areas on which the shading correction has been performed.

8. The imaging apparatus according to claim 7,
wherein the one or more processors are configured to determine a gain in the shading correction with reference to a maximum value of shading components in the image areas.

9. The imaging apparatus according to claim 7,
wherein the one or more processors are configured to determine a gain in the shading correction with reference to a median of shading components in the image areas.

10. A microscope system comprising:
the imaging apparatus according to claim 1;
the stage on which the object is placed; and
an objective lens provided so as to face the stage.

11. The microscope system according to claim 10, comprising the light source,
wherein the object is a specimen that is stained for fluorescence observation, and
wherein the light source is configured to generate excitation light for exciting the specimen.

12. An imaging method comprising:
controlling an image sensor to image an object within an imaging range to generate image data;
controlling a light source to generate light to be emitted in the imaging range;
controlling a field stop to adjust luminance distribution of the light such that the light continuously attenuates from an inner side toward an edge in a peripheral area within the imaging range;
controlling an actuator to move one or more of a stage on which the object is placed and the image sensor to sequentially move the imaging range relative to the object such that entire peripheral areas where the light attenuates overlap with each other in adjacent imaging ranges; and
sequentially obtaining, from the image sensor, the image data of a plurality of images with different imaging ranges and creating a combined image by stitching the plurality of images in such a way that adjacent images of the plurality of images corresponding to the adjacent imaging ranges are stitched together such that image areas corresponding to the entire peripheral areas overlap with each other.

13. A non-transitory computer-readable recording medium with an executable program stored thereon, the program instructing a processor to:
control an image sensor to image an object within an imaging range to generate image data;
control a light source to generate light to be emitted in the imaging range;
control a field stop to adjust luminance distribution of the light such that the light continuously attenuates from an inner side toward an edge in a peripheral area within the imaging range;
control an actuator to move one or more of a stage on which the object is placed and the image sensor to sequentially move the imaging range relative to the object such that entire peripheral areas where the light attenuates overlap with each other in adjacent imaging ranges; and
sequentially obtain, from the image sensor, the image data of a plurality of images with different imaging ranges and create a combined image by stitching the plurality of images in such a way that adjacent images of the plurality of images corresponding to the adjacent imaging ranges are stitched together such that image areas corresponding to the entire peripheral areas overlap with each other.

14. The imaging apparatus according to claim 1,
wherein the one or more processors are configured to:
determine a stage movement amount to move the imaging range relative to the object such that the entire peripheral areas where the light attenuates overlap with each other in adjacent imaging ranges; and
control the actuator to move the one or more of the stage on which the object is placed and the image sensor to sequentially move the imaging range relative to the object by the stage movement amount determined.

* * * * *